(12) United States Patent
Doudareva et al.

(10) Patent No.: US 11,198,884 B2
(45) Date of Patent: Dec. 14, 2021

(54) METHODS AND PLATFORMS FOR SUSTAINABLE HIGH YIELD TERPENOID PRODUCTION

(71) Applicants: Purdue Research Foundation, West Lafayette, IN (US); Salk Institute for Biological Studies, La Jolla, CA (US)

(72) Inventors: Natalia Doudareva, West Lafayette, IN (US); Joseph Noel, La Jolla, CA (US); Laura Henry, West Lafayette, IN (US); Suzanne T. Thomas, La Jolla, CA (US)

(73) Assignee: Purdue Research Foundation, West Lafayette, IN (US)

( * ) Notice: Subject to any disclaimer, the term of this patent is extended or adjusted under 35 U.S.C. 154(b) by 27 days.

(21) Appl. No.: 16/423,017

(22) Filed: May 26, 2019

(65) Prior Publication Data
US 2020/0370060 A1    Nov. 26, 2020

(51) Int. Cl.
*C12N 15/82* (2006.01)
*A01H 6/20* (2018.01)

(52) U.S. Cl.
CPC .......... *C12N 15/8216* (2013.01); *A01H 6/20* (2018.05); *C12N 15/8243* (2013.01)

(58) Field of Classification Search
CPC ............................................. C12N 15/8216
See application file for complete search history.

(56) References Cited

U.S. PATENT DOCUMENTS 9,051,555 B2    6/2015 Noel et al.

OTHER PUBLICATIONS

Saxena, B. et al., J Bioscience. vol. 39(1). Mar. 2014, pp. 33-41. (Year: 2014).*
Redding-Johanson, A.M. et al., (2011) Metabolic Engineering; vol. 13, pp. 194-203. (Year: 2011).*
Simkin, A.J. et al. Planta (2011) vol. 234; pp. 903-914. (Year: 2011).*
Hoshino, Y. and Gaucher, E.A. (2018) Mol. Biol. Evol. vol. 35, No. 9; pp. 2185-2197. (Year: 2018).*
Dellas N and Noel JP, Mutation of archaeal isopentenyl phosphate kinase highlights mechanism and guides phosphorylation of additional isoprenoid monophosphates, ACS Chemical Biology, Apr. 14, 2010, 589-601, vol. 5(6), USA.
Henry LK et al., Contribution of isopentyl phosphate to plant terpenoid metabolism, Nature Plants, Sep. 2018, 721-729, vol. 4, USA.
Henry LK et al., Supplementary Information to Contribution of isopentyl phosphate to plant terpenoid metabolism, Nature Plants, Sep. 2018, available at https://doi.org/10.1038/s41477-018-0220-z, USA.
Dellas N and Noel JP, Supporting Information for Mutation of archaeal isopentenyl phosphate kinase highlights mechanism and guides phosphorylation of additional isoprenoid monophosphates, ACS Chemical Biology, Apr. 14, 2010, 589-601, vol. 5(6), USA.

* cited by examiner

*Primary Examiner* — Russell Kallis
(74) *Attorney, Agent, or Firm* — Reichel Stohry Dean LLP; Natalie J. Dean; Mark C. Reichel

(57) ABSTRACT

Transgenic plants and methods for terpenoid production leveraging such transgenic plants are provided. Such transgenic plants may comprise a first heterologous nucleic acid encoding a polypeptide having 3-hydroxy-3-methylglutaryl-CoA reductase activity and a second heterologous nucleic acid encoding a polypeptide that introduces de novo formation of isopentenyl phosphate in the plant. Such de novo IP production may be achieved through the overexpression of phosphomevalonate decarboxylase in conjunction with 3-hydroxy-3-methylglutarylCoA reductase, which can result in up to a 130-fold increase of terpenoid production as compared to a wild-type plant.

20 Claims, 20 Drawing Sheets
Specification includes a Sequence Listing.

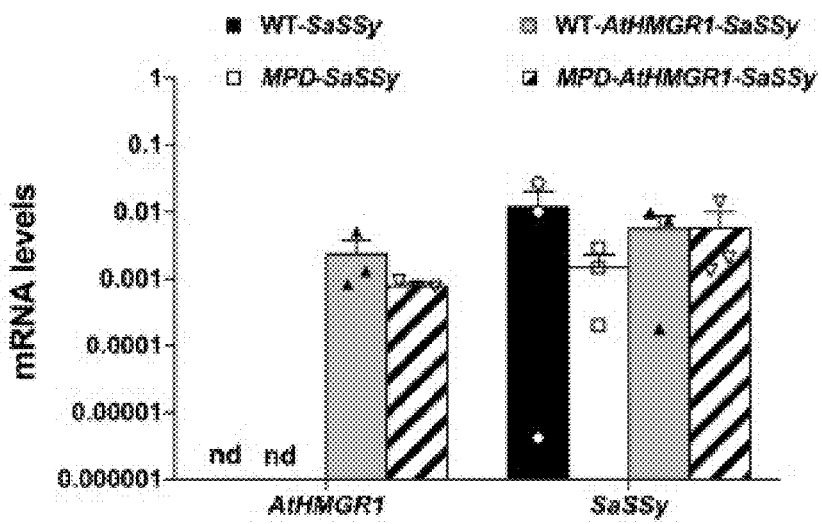
Figure 12A
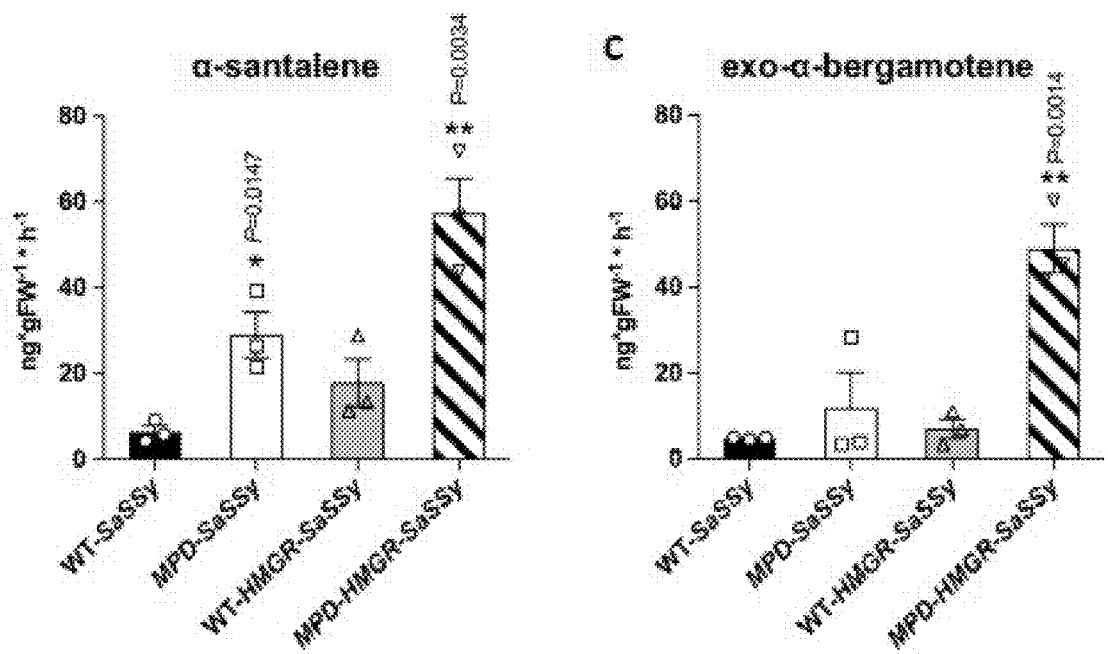
Figure 12B
Figure 12C

```
RcMPD    1 MYHRPLERMPGLATAIPAPYADLVERMATADADIRAALRAHGLTWEEYPOLTGAARERG 59
AtMDD1   1 MAEEKWVMVTAQTPTNIAVIKYWGKRDEVRILPINDS|TLTTVAVSPS 59
AtMDD2   1 MATEKWWFMVTAQTPTNIAVIKYWGKRDEVRILPVNDS|CTVTTVAVSPA 59
                                                      1301

RcMPD   60 AAAALAYPMQGVLKYHGLSDWDYRIAFLPSVSLCNDAGHTLTLVEFDPLATDCATING 118
AtMDD1  60 FDRDRMWLNGKEISLSGGSRYQNCLREIRSRADDVEDKEKGIKIAKKDWEKLHLHIASHN 118
AtMDD2  60 FDRDRMWLNGKEISLSGGSRYQNCLREIRGRAGDVEDMEKGIKIRKKDWEKLNLHIASHN 118

RcMPD  119 HVARGRELERVRQSLDAIRAASGATVRARVMSRNVTRGTRMGKGLGSSAAASAALALAA 177
AtMDD1 119 NFPTAAGLASSAAGFACLVFALAKLMNVNEDPSQLSAIARQGSGSACRSLFGGFVKWNM 177
AtMDD2 119 NFPTAAGLASSAAGFACLVFSLAKLMNVDEDPSHLSAIARQGSGSACRSLFGGFVKWTM 177

RcMPD  178 IAALYGDEAAANRRLVSCMARLLAGSGCRSAAGGCSIWFSSPGMPHEDSFAVRLDDAGQ 236
AtMDD1 178 GNKEDGSDSVAVQLVDDKHWQDLVIIAVVSSRQKETSSTSGMRESVETSLLLQHRAKE 236
AtMDD2 178 GSKEDGSDSVAVQLADEKHWQDLVI||AVVSSRQKETSSTSGMRESVETSLLLQHRAKE 236
                                       1302

RcMPD  237 LDDVRLITVPLDS HLDAPGSALFRCWMLSRRDEALACIAAARTGDWRTLG 295
AtMDD1 237 VVPVRILQMEEAIKNRDFTSFTKLTCSDSNQFHAVCMDTSPPIFYMNDTSHRIISLVEK 295
AtMDD2 237 VVPKRILQMEEAIKNRDFASFTQLTCTDSNQFHAVCLDTSPPIFYMNDTSHRIISLVEK 295

RcMPD  296 QWAELDSMRLHGITMSGSLENKLIGWEPENIVLFRMCNDLRSSGVPVYCSTDTGPTAVF 354
AtMDD1 296 VMNRSAGTPEIAYTFDAGPNAVMIARNRKVAVELLQGLLYCFPPKPDTDMKSYVLGDTSI 354
AtMDD2 296 VMNRSEGTPQVAYTFDAGPNAVLIARNRKVAVQLLQGLLYYFPPKSDTDMKSYVVGDNSI 354

RcMPD  355 ITHRDYEDAVVSAIEGLGLSLEAIRGRVAGPARLVDIAWAGGELGVAQ------ 402
AtMDD1 355 VKEAGLEGELPQGIKDKIGSQDKIGSQDKIGSQDQKGEVSYFICSRPGRGPVVLQDQTQALLHPQTGLPK 412
AtMDD2 355 LKEAGLDGASGVENLQPPPEIKDNIGSQDQKGEVSYFICTRPGKGPIVLHDQTQALLDP 413

RcMPD    : : : : :
AtMDD1   : : :
AtMDD2 414 ETGLPK
```

Figure 13g

SEQUENCE LISTING

<160> NUMBER OF SEQ ID NOS: 3

<210> SEQ ID NO 1
<211> LENGTH: 402
<212> TYPE: PRT
<213> ORGANISM: Roseiflexus castenholzii

<400> SEQUENCE: 1

```
Met Tyr His Arg Pro Leu Glu Arg Met Pro Gly Leu Ala Thr Ala Ile
1               5                   10                  15

Pro Ala Pro Tyr Ala Asp Leu Val Glu Arg Met Ala Thr Ala Asp Ala
            20                  25                  30

Asp Leu Arg Ala Ala Leu Arg Ala His Gly Leu Thr Trp Glu Glu Tyr
        35                  40                  45

Pro Asp Leu Thr Gly Ala Ala Arg Glu Arg Gly Ala Ala Ala Leu
    50                  55                  60

Ala Tyr Pro Met Gln Gly Val Leu Lys Tyr His Gly Leu Ser Asp Trp
65                  70                  75                  80

Asp Tyr Arg Ile Ala Phe Leu Pro Ser Val Ser Leu Cys Asn Asp Ala
                85                  90                  95

Gly His Thr Leu Thr Leu Val Glu Phe Asp Pro Asp Leu Ala Thr Asp
            100                 105                 110

Cys Ala Thr Ile Asn Gly His Val Ala Arg Gly Arg Glu Leu Glu Arg
        115                 120                 125

Val Arg Gln Ser Leu Asp Ala Ile Arg Ala Ala Ser Gly Ala Thr Val
    130                 135                 140

Arg Ala Arg Val Met Ser Arg Asn Val Thr Arg Gly Thr Arg Met Gly
145                 150                 155                 160

Lys Gly Leu Gly Ser Ser Ala Ala Ser Ala Ala Leu Ala Leu Ala
                165                 170                 175

Ala Ile Ala Ala Leu Tyr Gly Asp Glu Ala Ala Ala Asn Arg Arg Leu
            180                 185                 190

Val Ser Cys Met Ala Arg Leu Leu Ala Gly Ser Gly Cys Arg Ser Ala
        195                 200                 205

Ala Gly Gly Cys Ser Ile Trp Phe Ser Ser Pro Gly Met Pro His Glu
    210                 215                 220

Asp Ser Phe Ala Val Arg Leu Asp Asp Ala Gly Gln Leu Asp Asp Val
225                 230                 235                 240

Arg Leu Ile Thr Val Pro Leu Asp Ser Arg Ile Gly Leu Lys Thr Glu
                245                 250                 255

Gln Ala His Leu Asp Ala Pro Gly Ser Ala Leu Phe Arg Cys Trp Met
            260                 265                 270

Leu Ser Arg Arg Asp Glu Ala Leu Ala Cys Ile Ala Ala Ala Arg Thr
        275                 280                 285

Gly Asp Trp Arg Thr Leu Gly Gln Trp Ala Glu Leu Asp Ser Met Arg
    290                 295                 300

Leu His Gly Ile Thr Met Ser Gly Ser Leu Glu Asn Lys Leu Ile Gly
305                 310                 315                 320

Trp Glu Pro Glu Asn Ile Val Leu Phe Arg Met Cys Asn Asp Leu Arg
                325                 330                 335

Ser Ser Gly Val Pro Val Tyr Cys Ser Thr Asp Thr Gly Pro Thr Ala
            340                 345                 350

Val Phe Ile Thr His Arg Asp Tyr Glu Asp Ala Val Val Ser Ala Ile
        355                 360                 365
```

```
Glu Gly Leu Gly Leu Ser Leu Glu Ala Ile Arg Gly Arg Val Ala Gly
    370                 375                 380

Pro Ala Arg Leu Val Asp Ile Ala Trp Ala Gly Gly Glu Leu Gly Val
385                 390                 395                 400

Ala Asp

<210> SEQ ID NO 2
<211> LENGTH: 412
<212> TYPE: PRT
<213> ORGANISM: Arabidopsis thaliana

<400> SEQUENCE: 2

Met Ala Glu Glu Lys Trp Val Val Met Val Thr Ala Gln Thr Pro Thr
1               5                   10                  15

Asn Ile Ala Val Ile Lys Tyr Trp Gly Lys Arg Asp Glu Val Arg Ile
            20                  25                  30

Leu Pro Ile Asn Asp Ser Ile Ser Val Thr Leu Asp Pro Asp His Leu
        35                  40                  45

Cys Thr Leu Thr Thr Val Ala Val Ser Pro Ser Phe Asp Arg Asp Arg
    50                  55                  60

Met Trp Leu Asn Gly Lys Glu Ile Ser Leu Ser Gly Ser Arg Tyr Gln
65                  70                  75                  80

Asn Cys Leu Arg Glu Ile Arg Ser Arg Ala Asp Asp Val Glu Asp Lys
                85                  90                  95

Glu Lys Gly Ile Lys Ile Ala Lys Lys Asp Trp Glu Lys Leu His Leu
            100                 105                 110

His Ile Ala Ser His Asn Asn Phe Pro Thr Ala Ala Gly Leu Ala Ser
        115                 120                 125

Ser Ala Ala Gly Phe Ala Cys Leu Val Phe Ala Leu Ala Lys Leu Met
    130                 135                 140

Asn Val Asn Glu Asp Pro Ser Gln Leu Ser Ala Ile Ala Arg Gln Gly
145                 150                 155                 160

Ser Gly Ser Ala Cys Arg Ser Leu Phe Gly Gly Phe Val Lys Trp Asn
                165                 170                 175

Met Gly Asn Lys Glu Asp Gly Ser Asp Ser Val Ala Val Gln Leu Val
            180                 185                 190

Asp Asp Lys His Trp Asp Asp Leu Val Ile Ile Ala Val Val Ser
        195                 200                 205

Ser Arg Gln Lys Glu Thr Ser Ser Thr Ser Gly Met Arg Glu Ser Val
    210                 215                 220

Glu Thr Ser Leu Leu Leu Gln His Arg Ala Lys Glu Val Val Pro Val
225                 230                 235                 240

Arg Ile Leu Gln Met Glu Glu Ala Ile Lys Asn Arg Asp Phe Thr Ser
                245                 250                 255

Phe Thr Lys Leu Thr Cys Ser Asp Ser Asn Gln Phe His Ala Val Cys
            260                 265                 270

Met Asp Thr Ser Pro Pro Ile Phe Tyr Met Asn Asp Thr Ser His Arg
        275                 280                 285

Ile Ile Ser Leu Val Glu Lys Trp Asn Arg Ser Ala Gly Thr Pro Glu
    290                 295                 300

Ile Ala Tyr Thr Phe Asp Ala Gly Pro Asn Ala Val Met Ile Ala Arg
305                 310                 315                 320

Asn Arg Lys Val Ala Val Glu Leu Leu Gln Gly Leu Leu Tyr Cys Phe
                325                 330                 335
```

```
Pro Pro Lys Pro Asp Thr Asp Met Lys Ser Tyr Val Leu Gly Asp Thr
            340                 345                 350

Ser Ile Val Lys Glu Ala Gly Leu Glu Gly Glu Leu Pro Gln Gly Ile
        355                 360                 365

Lys Asp Lys Ile Gly Ser Gln Asp Gln Lys Gly Glu Val Ser Tyr Phe
    370                 375                 380

Ile Cys Ser Arg Pro Gly Arg Gly Pro Val Val Leu Gln Asp Gln Thr
385                 390                 395                 400

Gln Ala Leu Leu His Pro Gln Thr Gly Leu Pro Lys
                405                 410

<210> SEQ ID NO 3
<211> LENGTH: 419
<212> TYPE: PRT
<213> ORGANISM: Arabidopsis thaliana

<400> SEQUENCE: 3

Met Ala Thr Glu Lys Trp Val Phe Met Val Thr Ala Gln Thr Pro Thr
1               5                   10                  15

Asn Ile Ala Val Ile Lys Tyr Trp Gly Lys Arg Asp Glu Val Arg Ile
                20                  25                  30

Leu Pro Val Asn Asp Ser Ile Ser Val Thr Leu Asp Pro Asp His Leu
            35                  40                  45

Cys Thr Val Thr Thr Val Ala Val Ser Pro Ala Phe Asp Arg Asp Arg
        50                  55                  60

Met Trp Leu Asn Gly Lys Glu Ile Ser Leu Ser Gly Ser Arg Tyr Gln
65                  70                  75                  80

Asn Cys Leu Arg Glu Ile Arg Gly Arg Ala Gly Asp Val Glu Asp Met
                85                  90                  95

Glu Lys Gly Ile Lys Ile Arg Lys Lys Asp Trp Glu Lys Leu Asn Leu
            100                 105                 110

His Ile Ala Ser His Asn Asn Phe Pro Thr Ala Ala Gly Leu Ala Ser
        115                 120                 125

Ser Ala Ala Gly Phe Ala Cys Leu Val Phe Ser Leu Ala Lys Leu Met
    130                 135                 140

Asn Val Asp Glu Asp Pro Ser His Leu Ser Ala Ile Ala Arg Gln Gly
145                 150                 155                 160

Ser Gly Ser Ala Cys Arg Ser Leu Phe Gly Gly Phe Val Lys Trp Thr
                165                 170                 175

Met Gly Ser Lys Glu Asp Gly Ser Asp Ser Val Ala Val Gln Leu Ala
            180                 185                 190

Asp Glu Lys His Trp Asp Asp Leu Val Ile Ile Ala Val Val Ser
        195                 200                 205

Ser Arg Gln Lys Glu Thr Ser Ser Thr Ser Gly Met Arg Glu Ser Val
    210                 215                 220

Glu Thr Ser Leu Leu Leu Gln His Arg Ala Lys Glu Val Val Pro Lys
225                 230                 235                 240

Arg Ile Leu Gln Met Glu Glu Ala Ile Lys Asn Arg Asp Phe Ala Ser
                245                 250                 255

Phe Thr Gln Leu Thr Cys Thr Asp Ser Asn Gln Phe His Ala Val Cys
            260                 265                 270

Leu Asp Thr Ser Pro Pro Ile Phe Tyr Met Asn Asp Thr Ser His Arg
        275                 280                 285

Ile Ile Ser Leu Val Glu Lys Trp Asn Arg Ser Glu Gly Thr Pro Gln
    290                 295                 300
```

```
Val Ala Tyr Thr Phe Asp Ala Gly Pro Asn Ala Val Leu Ile Ala Arg
305                 310                 315                 320

Asn Arg Lys Val Ala Val Gln Leu Leu Gln Gly Leu Leu Tyr Tyr Phe
            325                 330                 335

Pro Pro Lys Ser Asp Thr Asp Met Lys Ser Tyr Val Val Gly Asp Asn
            340                 345                 350

Ser Ile Leu Lys Glu Ala Gly Leu Asp Gly Ala Ser Gly Val Glu Asn
        355                 360                 365

Leu Gln Pro Pro Glu Ile Lys Asp Asn Ile Gly Ser Gln Asp Gln
    370                 375                 380

Lys Gly Glu Val Ser Tyr Phe Ile Cys Thr Arg Pro Gly Lys Gly Pro
385                 390                 395                 400

Ile Val Leu His Asp Gln Thr Gln Ala Leu Leu Asp Pro Glu Thr Gly
            405                 410                 415

Leu Pro Lys
```

METHODS AND PLATFORMS FOR SUSTAINABLE HIGH YIELD TERPENOID PRODUCTION

BACKGROUND

Terpenoids, also referred to as isoprenoids, are one of the largest and most chemically diverse classes of primary and secondary metabolites in nature. All living organisms produce terpenoids and these compounds serve a broad range of physiological functions, including key roles in respiration, photosynthesis, modulating membrane fluidity, reproduction, regulating growth and development, defense, and environmental sensing and adaption. Some compounds that require targeting to membranes for their functions (like quinones, chlorophylls, and certain proteins) are anchored by terpenoid structures. In addition to their vital biological roles, terpenoids are also widely used—and highly valued—in a range of commercially useful products such as solvents, adhesives, coatings, synthetic intermediaries, flavorings and fragrances, biofuels, nutritional supplements, insecticides and pharmaceuticals.

Despite their structural diversity, all terpenoids begin with two universal five-carbon isoprene-like building blocks: isopentenyl diphosphate (IPP) and dimethylallyl diphosphate (DMAPP). Both IPP and DMAPP are derived from two independent routes—the mevalonic acid (MVA) and methylerythritol phosphate (MEP) pathways.

Interestingly, these pathways are not systematically distributed among the three domains of life (eukaryotes, archaea, and bacteria). For example, in plants, while the MEP pathway is exclusively localized in plastids, the MVA pathway is distributed between cytoplasm, endoplasmic reticulum, and peroxisomes. However, despite the two being compartmentally separated in the cell, metabolic cross-talk between these two pathways occurs via the exchange of IPP—and, to a lesser extent, DMAPP—in both directions.

IPP and DMAPP are subsequently used in multiple compartments by short-chain prenyltransferases to produce prenyl diphosphate intermediates, including geranyl diphosphate (GPP, $C_{10}$), farnesyl diphosphate (FPP, $C_{15}$), and geranylgeranyl diphosphate (GGPP, $C_{20}$). Whereas GPP synthases localize exclusively in plastids and provide precursors for monoterpenes, FPP synthases (FPPS) localize in cytosol and mitochondria and produce FPP for sesquiterpene, homoterpene, triterpene, sterol, brassinosteroid, and polyprenol biosynthesis. GGPP synthases reside in plastids, mitochondria, and the endoplasmic reticulum, and produce precursors for gibberellins, homoterpenes, carotenoids, phytyl side-chains for chlorophyll/tocopherols/quinones, polyprenols, oligoprenols, abscisic acid, and strigolactones, among others. Recently the present inventors have shown that there is a cytosolic pool of isopentenyl phosphate (IP), which can be phosphorylated to IPP and serves as a metabolically available carbon source for production of both mono- and sesquiterpenes.

In spite of the economic significance of the terpenoids and their many essential functions, there are many open questions about terpenoid metabolism and its regulation in plants. There are likely sophisticated biological control mechanisms in place that regulate the plant's production of these often structurally complex compounds. Furthermore, the origin of IP and possibly dimethylallyl phosphate (DMAP) in plants is unresolved (i.e. the precursors for IPP and DMAPP), leaving open questions about how the metabolism of the universal five-carbon terpenoid building blocks, IPP and DMAPP, are regulated in the plant kingdom.

Due to the complexities of terpenoid metabolism in plants, the capabilities of microbes producing terpenoids has been investigated. While some progress has been achieved in engineering terpenoid biosynthesis in microbes, this approach suffers from several drawbacks including dependence on exogenous carbon feedstocks, the toxicity of some terpenoids to their heterologous host, and the availability of often incomplete elucidated biosynthetic pathways for target product formation. In contrast, metabolic engineering in plants overcomes many of these issues using sustainable photosynthetic carbon fixation, complementation of unknown biosynthetic steps within terpenoid biosynthetic networks by endogenous plant enzymes, and sequestration and/or storage of terpenoids in specialized plant tissues and structures. Moreover, engineering of terpenoid production in crops often enhances natural plant defenses, thus serving as alternative pest and/or pathogen-management strategies. However, conventional approaches only manipulate the plastidial MEP pathway to increase terpenoid production in plants and have, at best, only see a modest increase in terpenoid production (e.g., at best, a 2-fold increase).

BRIEF SUMMARY

Transgenic plants are provided that overexpress at least two heterologous nucleic acids that significantly increase terpenoid biosynthesis in such transgenic plant. In at least one exemplary embodiment, a transgenic plant is provided that comprises a first heterologous nucleic acid encoding a polypeptide having 3-hydroxy-3-methylglutarylCoA reductase (HMGR) activity and (1) a second heterologous nucleic acid encoding a polypeptide that introduces de novo formation of isopentenyl phosphate (IP) in the transgenic plant, or (2) a polypeptide having phosphomevalonate kinase (PMK) activity. The polypeptide having HMGR activity and the polypeptide encoded by the second heterologous nucleic acid are overexpressed in the transgenic plant as compared to a corresponding wild-type plant.

In at least one embodiment, the first heterologous nucleic acid encoding a polypeptide having HMGR activity may be from *Arabidopsis*. One or both of the first and second heterologous nucleic acids may optionally be operably linked to a regulatory element for directing expression of the first and second heterologous nucleic acids. For example, and without limitation, such a regulatory element may comprise a tissue-specific promoter for directing expression of the first or second heterologous nucleic acid in the plant cells of a leaf, root, flower, developing ovule or seed of the transgenic plant. Further, the transgenic plant may be selected from the group consisting of: tobacco, rice, flax, wheat, barley, rye, corn, potato, pea, lettuce, cabbage, cauliflower, broccoli, turnip, radish, spinach, asparagus, onion, pepper, celery, squash, pumpkin, cucumber, strawberry, grape, raspberry, blackberry, pineapple, avocado, mango, banana, soybean, tomato, sorghum, sugarcane, algae, and any other land or water plant that is suitable for use in the disclosed systems and methods.

Where the polypeptide encoded by the second heterologous nucleic acid introduces de novo formation of IP in the transgenic plant and exhibits phosphomevalonate decarboxylase (MPD) activity, the second heterologous nucleic acid may, for example and without limitation, comprise a bacterial gene. There, in at least one exemplary embodiment, the transgenic plant can produce an increased amount of metabolically available IP relative to an amount of metabolically available IP produced in a corresponding wild-type plant due to such de novo formation of IP initiated by the second heterologous nucleic acid.

The transgenic plants of the present disclosure may also comprise a third heterologous nucleic acid comprising a sequence that encodes a synthase for catalyzing the formation of an exogenous terpenoid product of interest. There, the resulting transgenic plant expresses at least a portion of the exogenous terpenoid product of interest. In this manner, the transgenic plan can be designed to produce large amounts of a specific terpenoid(s) (either endogenous or exogenous) as needed.

In yet another exemplary embodiment of the transgenic plants of the present disclosure, the polypeptide encoded by the second heterologous nucleic acid may have or comprise PMK activity. There, monoterpene and sesquiterpene production of the transgenic plant may be at or near 20-fold greater and at or near 130-fold greater, respectively, than monoterpene and sesquiterpene production in the corresponding wild-type plant.

Methods for producing terpenoids using at least one transgenic plant of the present disclosure are also provided. In at least one exemplary embodiment, such a method for producing terpenoids using a transgenic plant comprising the steps of: providing a transgenic plant comprising a first heterologous nucleic acid encoding a polypeptide having HMGR activity and a second heterologous nucleic acid encoding a polypeptide having MPD or PMK activity such that the first and second heterologous nucleic acids are overexpressed in the transgenic plant as compared to a corresponding wild-type plant; and growing the transgenic plant under desired conditions such that one or more terpenoids of interest are produced. For example, in at least one embodiment, the transgenic plant is grown in the presence of labeled carbon dioxide, water, or a combination thereof; however, it will be understood that the transgenic plants may be grown under any suitable conditions whether now known or hereinafter developed.

Optionally, such methods may further comprise the step of isolating one or more terpenoids of interest from the transgenic plant after growth.

Transgenic plants resulting from the methods described herein can produce one or more terpenoids of interest at or over a 20-fold increase relative to terpenoid production of each terpenoid of interest in a corresponding wild-type plant.

In at least one embodiment, the step of providing a transgenic plant may further comprise the steps of: transforming plant cells with *Agrobacterium* containing a vector carrying the first heterologous nucleic acid encoding a polypeptide having HMGR activity in a context that allows for the overexpression of the first heterologous nucleic acid in a transgenic plant; transforming the plant cells with a gene containing a vector carrying the second heterologous nucleic acid encoding a polypeptide having PMK activity in a context that allows for the overexpression of the second heterologous nucleic acid in a transgenic plant; selecting transformants that overexpress both the first and second heterologous nucleic acids; and growing the transformants into a transgenic plant.

Additionally or alternatively, the methods of the present disclosure may comprise the step of transforming plant cells with a nucleic acid sequence operably linked to one or more regulatory elements for directing expression of the nucleic acid sequence in the plant cells, the nucleic acid sequence encoding a synthase for catalyzing the formation an exogenous terpenoid product of interest. Further, the step of selecting transformants that contain and overexpress both the first and second heterologous nucleic acids may further comprise selecting transformants that express at least a portion of the exogenous terpenoid product of interest.

Other embodiments provide methods for producing a transgenic plant cell culture. In at least one embodiment, such a method may comprise the steps of: obtaining transgenic plant cells by co-transforming plant cells with: a first heterologous nucleic acid encoding a polypeptide having HMGR activity and a second heterologous nucleic acid encoding a polypeptide having PMK activity; culturing a plurality of the transgenic plant cells; and selecting and isolating from the plurality of transgenic plant cells a subset of transgenic plant cells where expression of the first and second nucleic acids are amplified as compared to wild-type resulting in a transgenic plant cell culture. Furthermore, the method steps may additionally comprise the step of growing transgenic plant tissue from the subset of transgenic plant cells. In certain embodiments, the resulting transgenic plant cell culture produces β-caryophyllene and 5-epi-aristolochene at or near a 17-fold and a 63-fold increase, respectively, relative to β-caryophyllene and 5-epi-aristolochene emission in a corresponding wild-type plant cell culture.

In at least one embodiment, the step of obtaining transgenic plant cells may further comprise co-transforming the plant cells with a third nucleic acid comprising a sequence encoding a synthase for catalyzing the formation an exogenous terpenoid product of interest. Furthermore, the method may comprise the step of cultivating the transgenic plant cells so that at least a portion of the exogenous terpenoid product of interest encoded by the third nucleic acid is expressed by the transgenic cells. There, the subset of transgenic plant cells in the selecting and isolating step may also further comprise transgenic plant cells expressing at least a portion of the exogenous terpenoid product of interest.

STATEMENT OF SEQUENCE LISTING

The sequence presented herein (at least in FIG. 13g) is also provided in computer-readable form encoded in a file (68403 01SeqListing ST25.txt; file size: 12,288 bytes; date of creation: Apr. 26, 2021), which is herein incorporated by reference in its entirety. The information recorded in computer-readable form is identical to the written Sequence Listing provided herein, pursuant to 37 C.F.R. § 1.821(f).

BRIEF DESCRIPTION OF THE DRAWINGS

The disclosed embodiments and other features, advantages, and aspects contained herein, and the matter of attaining them, will become apparent in light of the following detailed description of various exemplary embodiments of the present disclosure. Such detailed description will be better understood when taken in conjunction with the accompanying drawings, wherein:

FIG. 11A shows a bar graph of levels of AtIPK and AtHMGR1 mRNAs in tobacco leaves of the RcMPD-4 transgenic line infiltrated with *Agrobacterium* carrying the empty vector control (MPD-EV) (black bars), the AtIPK construct (white bars), and the AtHMGR1 construct of the present disclosure (gray bars) and absolute transcript levels of AtIPK and AtHMGR1 are shown as picograms per 200 ng total RNA (means±s.e.m., n=3 biologically independent samples), and FIG. 11B shows a bar graph of sesquiterpene and monoterpene emission from RcMPD-4 transgenic tobacco leaves transiently overexpressing EV, AtIPK, and AtHMGR1, with all data means±s.e.m. (n=3 biologically independent samples); *P<0.05; **P<0.01; nd=not detected;

FIG. 12A displays data relating to levels of SaSSy and AtHMGR1 mRNAs in wild type and RcMPD-4 transgenic tobacco leaves infiltrated with *Agrobacterium* carrying SaSSy construct alone and AtHMGR1 construct with the SaSSy construct (absolute transcript levels of SaSSy and AtHMGR1 are shown as pg/mg total RNA (means±s.e.m., n=3 biologically independent samples);

FIGS. 12B and 12C display data relating to the emission of introduced santalenes (α-exo-bergamotene and α-santalene), with wild type and MPD-4 tobacco leaves used as genetic background for transient overexpression of AtHMGR1 and SaSSy in different combinations and shown on the y-axis (data are means±SEM, n=3 biologically independent samples; *P<0.05; **P<0.01 (two-tailed Student's t-test);

FIG. 13g shows the sequence alignment of RcMPD (SEQ ID NO: 1) with *Arabidopsis* AtMDD1 (SEQ ID NO: 2) and AtMDD2 SEQ ID NO: 3). SEQ ID NOS: 1-3 are also publicly available in the National Institutes of Health's genetic sequence database GenBank®. The identified putative PTS2 motifs AtMDD1 and AtMDD2 in SEQ ID NOS: 2 and 3, respectively, are labelled in box 1301. The traditional plant PTS2 signal, (R/K) (L/V/I) X5 (H/Q) (L/A) was identified in ReMPD in SEQ ID NO: 1 and is labeled in box 1302;

FIG. 14A shows levels of AtPMK and AtHMGR1 mRNAs in wild-type tobacco leaves infiltrated with *Agrobacterium* carrying the empty vector control (WT-EV) (black bars), the AtPMK construct (white bars), the AtHMGR1 construct (gray bars) and the AtPMK construct with the AtHMGR1 construct (dotted bars) (absolute transcript levels of AtPMK and AtHMGR1 are shown as picograms per 200 ng total RNA (means±s.e.m., n=3 biologically independent samples)); and FIG. 14B shows sesquiterpene and monoterpene emission from tobacco wild-type leaves transiently overexpressing EV, AtPMK, AtHMGR1, and AtPMK and AtHMGR1 together (all data are means±s.e.m., n=3 biologically independent samples, except n=6 biologically independent samples for WT-EV; *P<0.05; P<0.01; *P<0.001 (two-tailed Student's t-test)

Figure 1A:
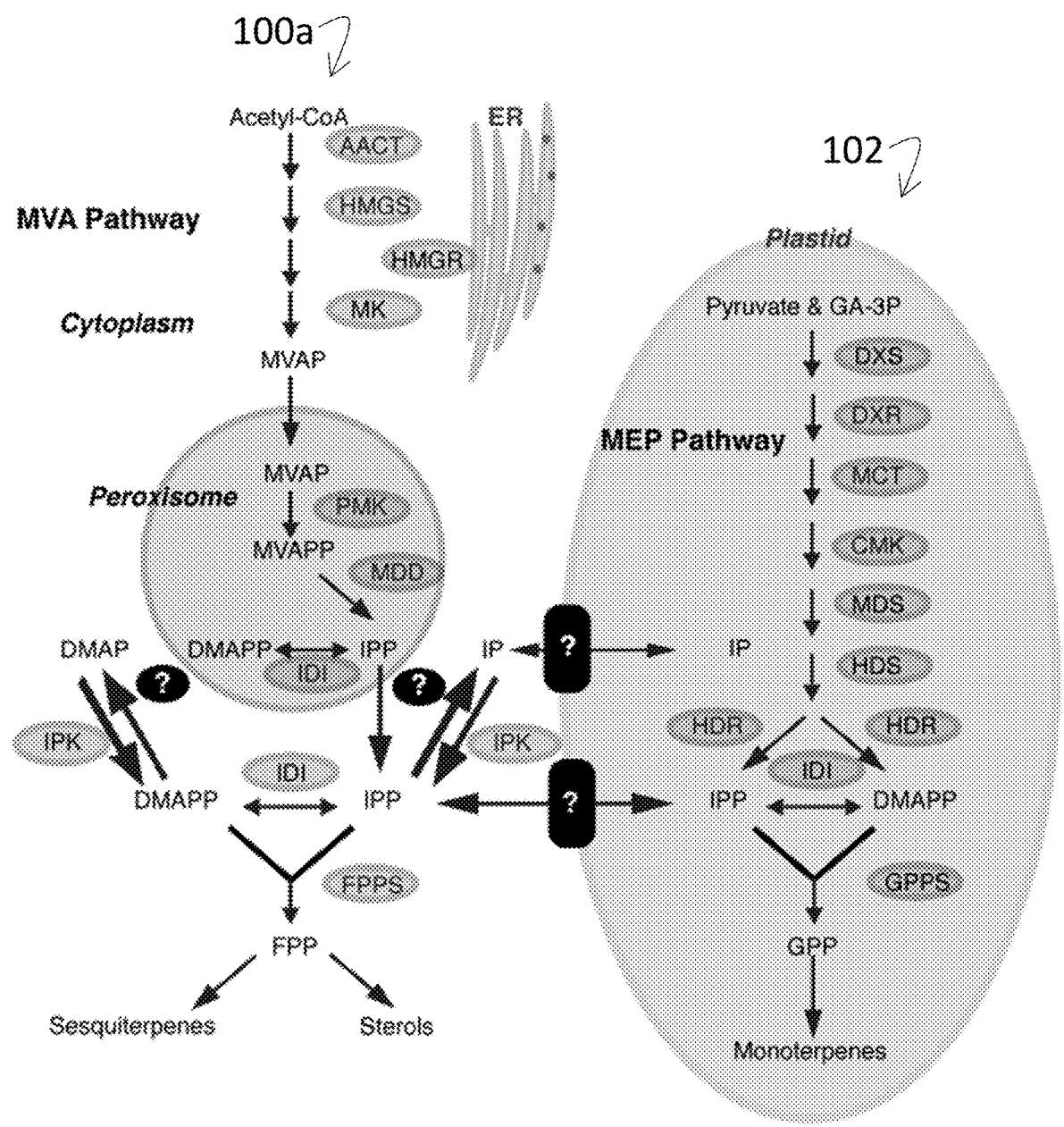
FIGS. 1A and 1B are graphical schematics of the terpenoid biosynthetic pathways in plants and in some archaea and bacteria.

While the present disclosure is susceptible to various modifications and alternative forms, exemplary embodiments thereof are shown by way of example in the drawings and are herein described in detail.

DETAILED DESCRIPTION

For the purposes of promoting an understanding of the principles of the present disclosure, reference will now be made to the embodiments illustrated in the drawings and specific language will be used to describe the same. It will nevertheless be understood that no limitation of scope is intended by the description of these embodiments. On the contrary, this disclosure is intended to cover alternatives, modifications, and equivalents as may be included within the spirit and scope of this application as defined by the appended claims. As previously noted, while this technology may be illustrated and described in one or more preferred embodiments, the compositions, systems and methods hereof may comprise many different configurations, forms, materials, and accessories.

In the following description, numerous specific details are set forth in order to provide a thorough understanding of the present disclosure. Particular examples may be implemented without some or all of these specific details and it is to be understood that this disclosure is not limited to particular biological systems, which can, of course, vary.

Various techniques and mechanisms of the present disclosure will sometimes describe a connection or link between two components. Words such as attached, linked, coupled, connected, and similar terms with their inflectional morphemes are used interchangeably, unless the difference is noted or made otherwise clear from the context. These words and expressions do not necessarily signify direct connections, but include connections through mediate components and devices. It should be noted that a connection between two components does not necessarily mean a direct, unimpeded connection, as a variety of other components may reside between the two components of note. Consequently, a connection does not necessarily mean a direct, unimpeded connection unless otherwise noted.

Furthermore, wherever feasible and convenient, like reference numerals are used in the figures and the description to refer to the same or like parts or steps. The drawings are in a simplified form and not to precise scale. It is understood that the disclosure is presented in this manner merely for explanatory purposes and the principles and embodiments described herein may be applied to devices and/or system components that have dimensions/configurations other than as specifically described herein. Indeed, it is expressly contemplated that the size and shapes of the composition and system components of the present disclosure may be tailored in furtherance of the desired application thereof.

Unless defined otherwise, all technical and scientific terms used herein have the same meaning as commonly understood by one of skill in the relevant arts. Although any methods and materials similar to or equivalent to those described herein can be used in the practice or testing of the subject of the present application, the preferred methods and materials are described herein. Additionally, as used in this specification and the appended claims, the singular forms "a", "an" and "the" include plural referents unless the content clearly dictates otherwise. Thus, for example, reference to "a tRNA" includes a combination of two or more tRNAs; reference to "bacteria" includes mixtures of bacteria, and the like.

Further, as used herein, the terms "gene overexpression" and "overexpression" (when used in connection with a gene) have the meaning ascribed thereto by one of ordinary skill in the relevant arts, which includes (without limitation) the overexpression or misexpression of a wild-type gene product that may cause mutant phenotypes and/or lead to abundant target protein expression.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, that are synthetic, naturally occurring, and non-naturally occurring, have similar binding properties as the reference nucleic acid, and metabolized in a manner similar to the reference nucleotides. Examples of such analogs include, without limitation, phosphorothioates, phosphoramidates, methyl phosphonates, chiral-methyl phosphonates, 2-O-methyl ribonucleotides, and peptide-nucleic acids.

The terms "polypeptide," "peptide," and "protein" are used interchangeably herein to refer to a polymer of amino acid residues, a polypeptide, or a fragment of a polypeptide, peptide, or fusion polypeptide. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function in a manner similar to the corresponding naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e. a carbon that is bound to a hydrogen, a carboxyl group, an amino group, and an R group (e.g., homoserine, norleucine, methionine sulfoxide, methionine methyl sulfonium). Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, the term "regulatory element" means and includes, in its broadest context, a polynucleotide molecule having gene regulatory activity, i.e. one that has the ability to affect the transcription or translation of an operably linked transcribable polynucleotide molecule. Indeed, regulatory elements comprise a series of nucleotides that determines if, when, and at what level a particular gene is expressed. Regulatory elements such as promoters, leaders, introns and transcription termination regions are polynucleotide molecules having gene regulatory activity that play an integral part in the overall expression of genes in living cells. Promoters may be derived from a classical eukaryotic genomic gene, including (without limitation) the TATA box often used to achieve accurate transcription initiation, with or without a CCAAT box sequence and additional regulatory or control elements (i.e. upstream activating sequences, enhancers, and silencers) or may be the transcriptional regulatory sequences of a classical prokaryotic gene. The term "promote" may also be used herein to describe a synthetic or fusion molecule, or derivative that confers, activates, or enhances expression of a nucleic acid molecule in a cell, tissue, or organ. Promoters may contain additional copies of one or more specific regulatory elements to further enhance expression and/or to alter the spatial expression and/or temporal expression of a nucleic acid molecule, or to confer expression of a nucleic acid molecule to specific cells or tissues such as meristems, leaves, roots, embryo, flowers, seeds or fruits (i.e. a tissue-specific promoter). In the context of the present invention, a promoter preferably is a plant-expressible promoter sequence, meaning that the promoter sequence (including any additional regulatory elements added thereto or contained therein) is at least capable of inducing, conferring, activating, or enhancing expression in a plant cell, tissue or organ. Promoters that also function or solely function in non-plant cells such as bacteria, yeast cells, insect cells, and animal cells, however, are not excluded from the invention hereof.

As used herein, the term "operably linked" means a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter modulates transcription of the gene of interest in a cell.

The terms "terpenoids" and "terpenes" are used interchangeably herein as the inventive disclosure is generically applicable to both. Chemically, terpenes are derived from one or more isoprene unit(s), also designated as prenyl units. By conjugation of heteroatoms such as, e.g., oxygen or nitrogen, terpenes can be modified to terpenoids that are also known as isoprenoids.

As used herein, the term "transgenic plants" refers to plants and plant cells that have incorporated DNA sequences including, but not limited to genes that are perhaps not normally present, DNA sequences not normally transcribed into RNA or translated into a protein ("expressed"), or any other genes or DNA sequences that one desires to introduce into the non-transformed plant, but which one desires to either genetically engineer or to have altered expression. It is contemplated that in some instances the genome of transgenic plants of the present invention will have been augmented through the stable introduction of the transgene; however, in other instances, the introduced gene will replace an endogenous sequence. A transgenic plant includes a plant regenerated from an originally-transformed plant or cell of the present disclosure and progeny transgenic plants from later generations or crosses of a transformed plant described herein.

The novel transgenic plants and methods of the present disclosure are broadly directed toward transgenic plants, and methods of leveraging such inventive transgenic plants, to produce terpenoids or isoprenes in amounts significantly greater than those produced by a corresponding wild-type plant and/or as heretofore been possible using conventional methodologies. In at least one embodiment, the transgenic plants, platforms, and inventive methods of the present disclosure provide for at least a 20-50 fold greater increase in terpenoid production as compared to the wild-type plant. In at least one embodiment, the inventive transgenic plants, platforms, and methodologies of the present disclosure increase the metabolically available isopentenyl phosphate (IP), which results in measurable changes in terpene products derived from both the methylerythritol phosphate (MEP) and mevalonate (MVA) pathways. As explained in further detail below, this is achieved through a novel manipulation of the cytosolic MVA pathway in conjunction with introducing de novo IP formation through the overexpression of one or more bacterial genes that encode enzymes for catalyzing a rate-limiting step of the alternate MVA pathway (e.g., bacterial phosphomevalonate decarboxylase (MPD)).

Further, in view of the novel findings disclosed herein, previously unpredicted peroxisomal localization of bacterial MPD led to the discovery that the step catalyzed by phosphomevalonate kinase (PMK) in the classical MVA pathway imposes a hidden constraint on the flux therethrough. These complementary findings fundamentally alter conventional views of metabolic regulation of terpenoid metabolism in plants and provide novel metabolic engineering targets for the production of high-value terpenes in plants. Certain embodiments of the inventive transgenic plants, platforms, and methods provided herein also increase PMK availability and, thus, increase downstream flux through the classical MVA pathway which can result in a significant increase in IP production and thereafter terpenoid production.

While many of the transgenic plants in the examples set forth herein are tobacco plants, because plants have a common MVA pathway, the description of the present disclosure is applicable to all plants and the inventive transgenic plants, platforms and methods presented herein may be (or may be used in connection with) any plant or plant cell that may be transformed with the desired nucleic acid sequences. For example, and without limitation, the present disclosure is applicable to at least tobacco, rice, flax, wheat, barley, rye, corn, potato, pea, lettuce, cabbage, cauliflower, broccoli, turnip, radish, spinach, asparagus, onion, pepper, celery, squash, pumpkin, cucumber, strawberry, grape, raspberry, blackberry, pineapple, avocado, mango, banana, soybean, tomato, sorghum, and sugarcane plants, and even algae (as, like land plants, algae have both the MVA and MEP pathways which act as the gatekeepers to the various branches of terpenoid biosynthesis in both land plants and algae).

As previously described, despite their structural diversity, all terpenoids begin with two universal five-carbon isoprene-like building blocks, isopentenyl diphosphate (IPP) and dimethylallyl diphosphate (DMAPP), which may be derived from two different routes: the mevalonic acid (MVA) and methylerythritol phosphate (MEP) pathways. Now referring to FIG. 1A, flow charts representative of the classical MVA pathway 100a and the MEP pathway 102 are shown. Further, FIG. 1B depicts a flow chart representative of an alternative MVA pathway 100b that is present in some bacteria and archaea (e.g., the Chloroflexi phylum).

The MVA pathway 100a generates IPP and DMAPP, which are elongated by the ubiquitous enzymes farnesyl diphosphate synthases (FPPSs). Generally, FPPSs catalyze the condensation of one DMAPP molecule with two IPP molecules to produce farnesyl diphosphate (FPP) and two molecules of pyrophosphate. FPP is an essential metabolite used for sesquiterpene, homoterpene, triterpene, sterol, brassinosteroid, and polyprenol biosynthesis. It was conventionally thought that HMGR catalyzes the rate-limiting step of the MVA pathway within the cytoplasm; however, conventional strategies that employ HMGR-overexpression-based metabolic engineering alone do not achieve high-yield terpenoid production in plants. Instead, as supported by the present disclosure and data set forth herein, the MVA pathway 100a is regulated by additional—and conventionally undetermined—mechanisms that govern flow through the pathway and subsequently metabolite yield.

It has recently been determined that in addition to the classical MVA and MEP pathway enzymes, plant genomes encode another IPP-generating protein: isopentenyl phosphate kinase (IPK). In plants, IPK localizes in the cytoplasm, where it transforms isopentenyl phosphate (IP) and possibly dimethylallyl phosphate (DMAP) to IPP and DMAPP via ATP-dependent phosphorylation. IPK appears to augment terpenoid production through both the MVA and MEP pathways 100a, 100b, 102.

Figure 1B:
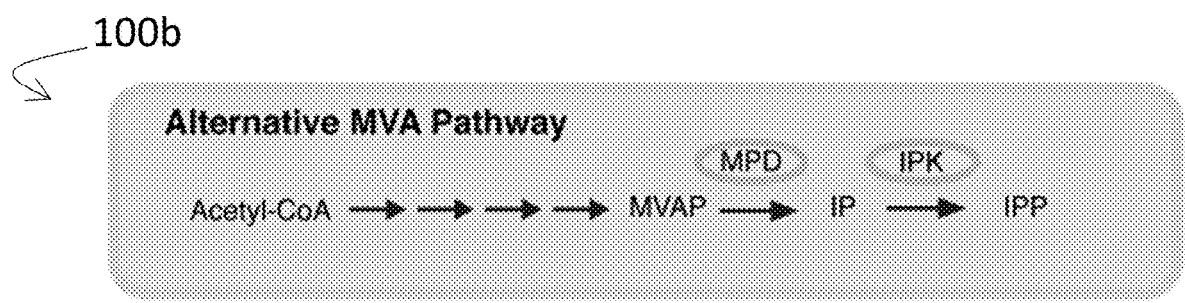

While, in plants, IPK is involved in a metabolite reactivation process, in some bacteria and archaea, IPK catalyzes an essential and final step in the alternative MVA pathway 100b (see FIG. 1B). The alternative MVA pathway 100b bifurcates from the classical metabolic route 102 following mevalonate kinase (MK)-mediated phosphorylation of mevalonate yielding phosphomevalonate (MVAP). In the classical MVA pathway 100a, MVAP undergoes phosphorylation catalyzed by phosphomevalonate kinase (PMK) to produce mevalonate diphosphate (MVAPP), which is subsequently subjected to decarboxylation catalyzed by mevalonate 5-diphosphate decarboxylase (MDD) (see FIG. 1A). In contrast, in the alternative MVA pathway 100b, the order of reactions is reversed. MVAP undergoes initial decarboxylation to IP (catalyzed by a MPDD), which is followed by ATP-dependent phosphorylation of IP (catalyzed by IPK).

The presence of genes encoding IPK in all sequenced plant genomes supports that modulating the ratios of IP to IPP and DMAP to DMAPP plays a role in regulating terpenoid biosynthesis. Moreover, as described in further detail below, a significant yield enhancement of MVA and MEP pathway-derived terpenoids was achieved upon overexpression of *Arabidopsis thaliana* IPK (AtIPK) in tobacco leaves, which further supports the contribution of IP formation to regulating the plant terpenoid network. On the other hand, the absence of genes encoding MPDs in plant genomes indicates that, in plants, IP and possibly DMAP arise via a different route than the alternative MVA pathway 100b.

In part, this disclosure and the data presented herein show that Nudix hydrolases function as a part of key regulatory machinery capable of modulating the metabolic outcome of terpenoid metabolic networks in plants. Furthermore, the data presented herein demonstrates that IP and possibly DMAP in plants are not produced de novo, nor result from the cumulative effects of nonspecific phosphatase activity. Instead, IP and possibly DMAP originate from the active dephosphorylation of IPP (DMAPP) by dedicated Nudix hydrolases that, together with IPK, coordinately regulate the concentration of the IPP destined for higher-order terpenoid biosynthesis. These findings highlight the significance of IPK in plant metabolism and support that these Nudices, in particular Nudx3, are not just dephosphorylating isoprenoid building blocks.

The inventive transgenic plants, platforms, and methods of the present disclosure leverage these findings and allow for unprecedented isoprenoid/terpenoid biosynthesis rates— in some cases over a 130-fold increase over like terpene production in a corresponding wild-type plant. In at least one embodiment, such transgenic plants, platforms, and methods increase metabolically available IP by overexpression of a bacterial MPD, which results in a measurable uptick in terpene products produced (i.e. both in monoterpenes and sesquiterpenes). Moreover, as described below in additional detail, the unpredicted peroxisomal localization of bacterial MPD led to the discovery that the step catalyzed by PMK imposes a hidden constraint on flux through the classical MVA pathway 100a. Accordingly, additional embodiments of the present disclosure utilize the overexpression of PMK to further increase the production of high-value terpenes by plants.

EXAMPLES

The following examples illustrate certain specific embodiments of the invention and are not meant to limit the scope of the invention in any way.

Example 1

Introducing De Novo IP Formation Through the Overexpression of a Bacterial RcMPD in Tobacco To identify IPP/DMAPP phosphatase candidates that may produce IP/DMAP in planta, a certain unique two-domain (hydrolase/peptidase) member of the Nudix hydrolase superfamily, AtNudx3 (At1g79690), was considered. While data supports that AtNudx3 can dephosphorylate IPP and hydrolyze dipeptide substrates in vitro, to date, it has been difficult to determine Nudix enzymes' physiological function due to their measurable in vitro substrate promiscuity.

Primarily, the plant material used to generate the transgenic lines and transient expression in the studies described herein comprised N. tabacum cv. Xanthi was used for generation of transgenic lines and transient expression because tobacco plants have the advantages of being easily transformed and easy to grow. However, it is noted that the results of the studies presented herein are not limited in their applicability to N. tabacum as all plants have a common MVA pathway 100a. As such, it is understood that the results of these studies (as well as the inventive transgenic plants, systems, and methodologies derived therefrom and presented herein) are not limited to N. tabacum, but instead may comprise any plant or crop.

Arabidopsis T-DNA insertion mutant lines, nudx1-1 (SALK 025320C), nudx1-2 (SAIL_236_D10), nudx3-1 (SAIL_554_G07), and nudx3-2 (SALK 009963), were obtained from the Arabidopsis Biological Resource Center. Homozygosity of obtained mutant lines were verified by PCR on isolated genomic DNA using respective gene- and T-DNA Express Primer Design (Salk Institute). All plant material was grown in a greenhouse or growth room under a 16 h light/8 h dark photoperiod.

To identify putative IPP/DMAPP phosphatase candidates that produce IP/DMAP in planta, all Nudix enzymes encoded by the Arabidopsis genome in E. coli were expressed. The open reading frames (ORFs) of Arabidopsis Nudix genes were PCR-amplified from cDNA with gene-specific forward and reverse primers, with the exception of AtNudx3, which was obtained from the Arabidopsis Biological Resource Center (clone U16680). Transit peptide sequences were excluded when present.

ORFs were cloned into a modified pET28b vector with an N-terminal His8-tag by the In-Fusion cloning system (Takara Bio USA). ORFs for Nudix 4, 8-11, 16-18, 21-24, and 26 were also cloned into cold-shock expression vector pCold I DNA (Takara Bio USA). The resulting constructs were transformed into BL21(DE3) E. coli and grown in terrific broth medium supplemented with 50 μg ml$^{-1}$ kanamycin or 100 μg ml$^{-1}$ ampicillin. Protein expression was induced with 0.5 mM isopropyl 1-thio-β-D-galactopyranoside at 18° C. for pET28b or 15° C. for pCold I DNA. After 20-24 hours of incubation, cells were collected by centrifugation and lysed by sonication in 50 mM Tris-HCL pH 8.0 buffer, 0.5 M NaCl, 20 mM imidazole and 10% glycerol.

After removal of the cell debris by centrifugation, expressed proteins were purified from the supernatants by immobilized metal-affinity chromatography with HisPur Ni-NTA resin (ThermoFisher Scientific). Pure proteins were eluted with 50 mM Tris-HCL pH 8.0, 0.5 M NaCl buffer supplemented with 250 mM imidazole followed by buffer exchange to 50 mM Tris-HCl pH 8.0 and 0.2 M NaCl for storage. For the crystal screening and steady-state kinetic analysis described below, the N-terminal His8-tags of AtNudx1 and AtNudx3 were removed with thrombin and remaining histidine-tagged protein was removed by passing over HisPur Ni-NTA resin. AtNudx1 and AtNudx3 were further purified by size-exclusion chromatography on a Superdex 200 16/60 column (GE Lifesciences) equilibrated and eluted with 50 mM Tris-HCl pH 8.0 supplemented with 0.2 M NaCl and 2 mM dithiothreitol.

Of the 27 heterologously expressed proteins, 16 produced soluble enzymes that were assayed for small molecule phosphatase activity (the remaining genes, AtNudx 2, 4, 8, 10, 13, 16-19, 21, and 22 produced insoluble inclusion bodies and were not assayed). Most of these Nudix enzymes were previously assayed against a panel of phosphate-bearing substrates; however, isoprenoid diphosphates were notably absent.

Figure 2A:
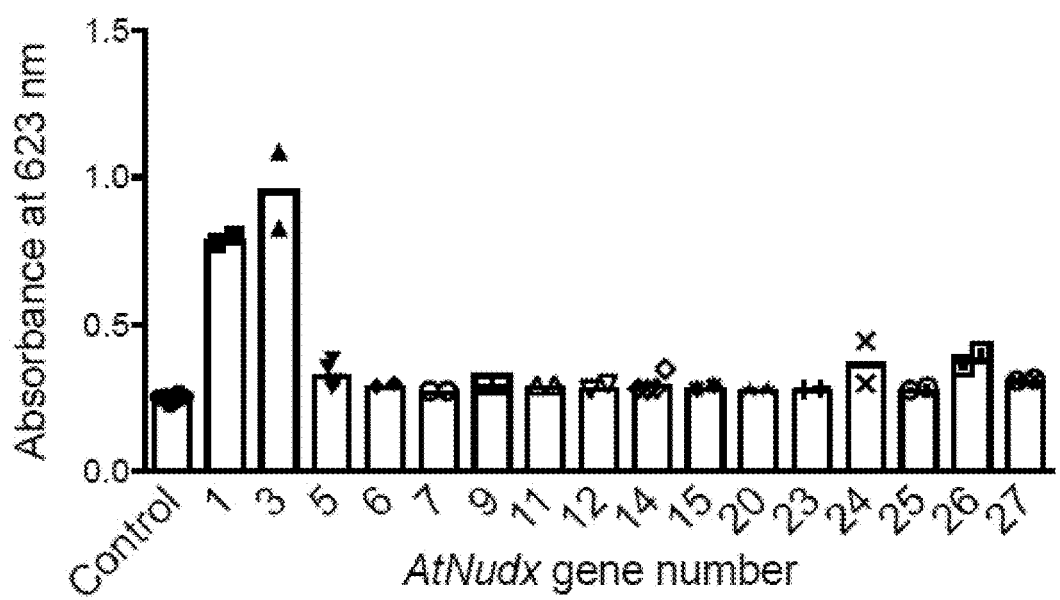
FIG. 2A shows a bar graph depicting the results of BIOMOL Green end-point assays detecting free phosphate, where the assays were conducted with 0.1 µM purified Nudx enzyme, 0.1 mM IPP, 10 mM $MgCl_2$, and 0.1 M TAPS pH 8.5 at 37° C., quenched after one hour by the addition of BIOMOL Green and phosphate detected at 623 nm; data presented are means of independent biological experiments where n=8 for AtNudx1, AtNudx3, AtNudx6, AtNudx7, AtNudx9, AtNudx11, AtNudx12, AtNudx15, AtNudx20, AtNudx23, AtNudx24, AtNudx25, AtNudx26, and AtNudx27.
Figure 2B:
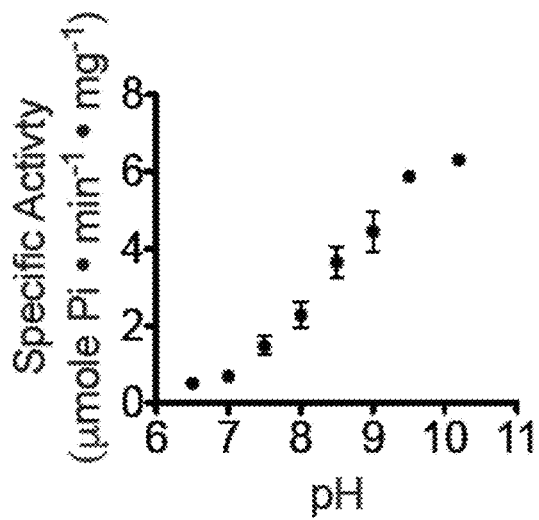
FIG. 2B shows a results of assay optimization for *A. thaliana* Nudx1 (subpart 1 and subpart 2) and Nudx3 (subpart 3 and subpart 4), with subparts 1 and 3 representative of pH optimum and subparts 2 and 4 representative of $Mg^{2+}$ dependence and where the assays were conducted at 37° C. with 0.1 mM IPP and 50 nM AtNudx1 or 25 nM AtNudx3, no activity was observed with $CaCl_2$) and $ZnCl_2$ for both enzymes and data are means±SD (n=3 independent experiments)
Figure 2B:
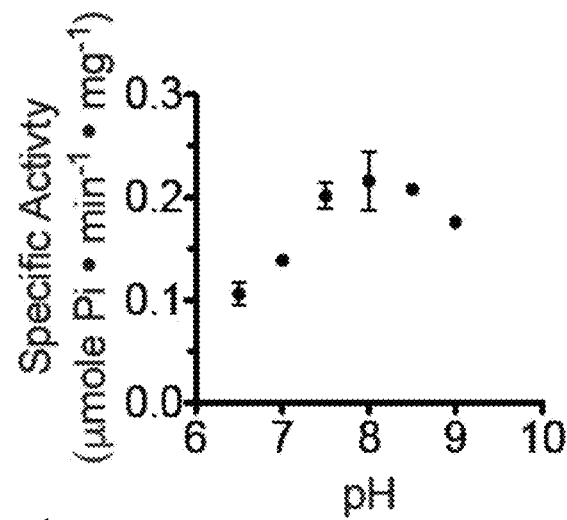
Figure 2B:
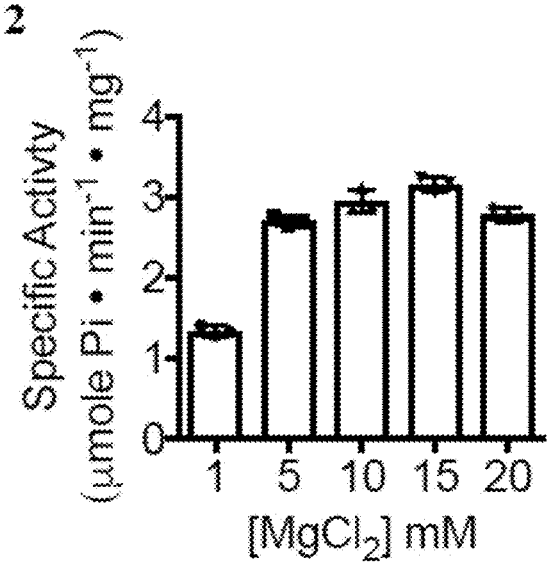
Figure 2B:
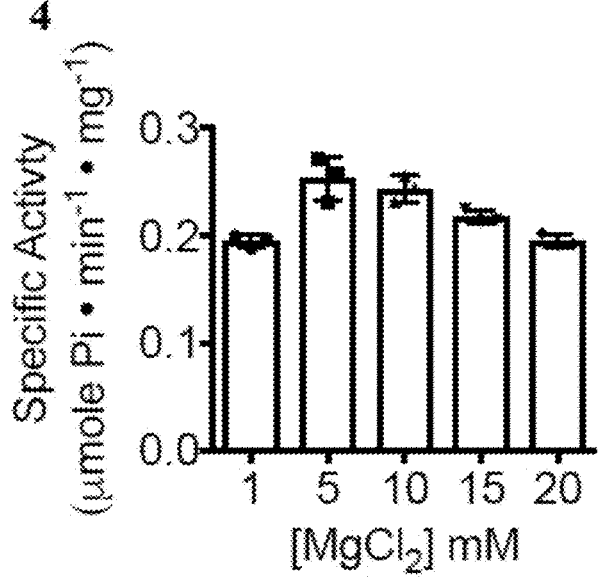

The soluble enzymes identified were then screened for catalytic activity with IPP as a substrate using a modified malachite green assay for free phosphate detection. As shown in the bar graph shown in FIG. 2A, only AtNudx1 (At1g68760) and AtNudx3 efficiently catalyzed dephosphorylation of IPP to IP, while the remaining enzymes exhibited low to no activity. Thereafter, the AtNudx1 and AtNudx3 assays were optimized for pH and magnesium cation ($Mg^{2+}$) dependence (see FIG. 2B), steady state kinetic constants were determined for AtNudx1 and AtNudx3 using isoprenoid mono- and di-phosphate containing compounds. Both AtNudx1 and AtNudx3 catalyzed dephosphorylation of MVAPP, IPP, DMAPP, geranyl diphosphate (GPP), and FPP to the monophosphate products, MVAP, IP, DMAP, geranyl phosphate (GP), and farnesyl phosphate (FP), respectively, and did not catalyze further dephosphorylation to their respective isoprenoid alcohols. AtNudx1 utilized IPP, DMAPP, GPP, and FPP with equal catalytic efficiencies, while MVAPP was 100-fold less efficient as a substrate (Table 1). In contrast, AtNudx3 preferred IPP and DMAPP with catalytic efficiencies similar to AtNudx1 and with 3-fold higher catalytic efficiencies compared to AtNudx1 using GPP and FPP as substrates (Table 1).

TABLE 1

Kinetic parameters for recombinant *A. thaliana* Nudx1 and Nudx3.

| | AtNudx1 | | | AtNudx3 | | |
|---|---|---|---|---|---|---|
| Substrate | $K_M$ (μm) | $k_{cat}$ ($s^{-1}$) | $k_{cat}/K_M$ ($M^{-1}\,s^{-1}$) | $K_M$ (μm) | $k_{cat}$ ($s^{-1}$) | $k_{cat}/K_M$ ($M^{-1}\,s^{-1}$) |
| (R)-MVAPP | 240 ± 60 | 0.51 ± 0.06 | $2.1 \times 10^3$ ± 0.6 | 125 ± 36 | 1.5 ± 0.2 | $1.2 \times 10^4$ ± 0.4 |
| DMAPP | 10.7 ± 1.8 | 1.7 ± 0.07 | $1.6 \times 10^5$ ± 0.3 | 44 ± 8 | 7.1 ± 0.3 | $1.6 \times 10^5$ ± 0.3 |
| IPP | 8.0 ± 0.6 | 1.11 ± 0.02 | $1.4 \times 10^5$ ± 0.1 | 36 ± 8 | 5.5 ± 0.3 | $1.5 \times 10^5$ ± 0.3 |
| GPP | 8.3 ± 2.5 | 2.0 ± 0.3 | $2.5 \times 10^5$ ± 0.8 | 53 ± 13 | 2.7 ± 0.3 | $5.1 \times 10^4$ ± 0.5 |
| FPP | 8.7 ± 1.6 | 1.35 ± 0.06 | $1.6 \times 10^5$ ± 0.3 | 58 ± 10 | 3.3 ± 0.3 | $5.7 \times 10^4$ ± 0.5 |
| 8-oxo-dGTP | 33 ± 2 | 4.5 ± 0.1 | $1.4 \times 10^5$ ± 0.1 | NA | NA | NA |

Data are means ± SD (n = 3 independent experiments).
NA, no detectable activity.
No phosphatase activity was detected for AtNudx1 and AtNudx3 with IP, DMAP, MVAP, GP, and FP.

Example 2

AtNudx1 Activity Against 8-Oxo-dGTP is Likely to be Irrelevant In Vivo

AtNudx1 functions as an 8-oxo-dGTPase based upon homology with bacterial and mammalian Nudix superfamily members. While AtNudx3 was unable to dephosphorylate 8-oxo-dGTP in the above-described studies, AtNudx1 catalyzed dephosphorylation with catalytic efficiencies similar to those obtained with IPP and DMAPP as substrates (see Table 1). However, AtNudx1 only weakly prefers 8-oxo-dGTP as compared to dGTP with $(k_{cat}/K_M)^{8-oxo-dGTP}/(k_{cat}/K_M)^{dGTP}=2.6^{20}$, while intracellular concentrations of dGTP are expected to be significantly higher than 8-oxo-dGTP.

To precisely define the structural basis for substrate selectivities of AtNudx1, diffraction quality crystals were obtained for atomic resolution protein x-ray crystallographic analyses. Crystallization trials were conducted by the hanging-drop method using Hampton Research crystal screens. Typically, 1 μl of protein at 12 mg ml$^{-1}$ in 50 mM Tris-HCL pH 8.0, 0.2 M NaCl and 2 mM dithiothreitol was mixed with 1 μl of each reservoir solution and incubated at 4° C. over a 500 μl reservoir solution.

Ligand-bound structures were obtained by co-crystallization with 5-10 mM ligand. Diffraction-quality AtNudx1 crystals were obtained from a mixture of the protein with 0.1 M succinct acid pH 5.0, 20% PEG 4000 and 0.3 M Mg(NO$_3$)$_2$. Crystals were flash-frozen in cryoprotectant of 17% ethylene glycol and reservoir buffer plus substrate.

X-ray diffraction data was collected at beamlines 8.2.1 and 8.2.2 of the Advanced Light Source at Lawrence Berkeley National Laboratory. Diffraction images were indexed and integrated with iMosflm, and the measured reflection intensities were scaled and merged using CCP4 Aimless. The initial structural elucidation of AtNudx1 was obtained by molecular replacement with CCP4 MolRep using a search model derived from *Rickettsia Felis* MutT (pbd entry 4KYX) with non-conserved amino-acid residues pruned using the CPP4 Chainsaw program. The structural model was refined with Phenix Refine and inspected against electron-density maps and adjusted manually in Coot (a model-building tool for molecular graphics). Autobuilding was performed with Phenix Autobuild (an iterative model building, structure refinement and density modification tool). Subsequent structure determinations of other forms of AtNudx1, which were crystallized isomorphously, were initiated with the refined AtNudx1 model, after omission of ligands and water molecules.

TABLE 2

X-ray Diffraction Data Collection and Refinement Statistics.

| | AtNudx1 | AtNudx1 · IPP |
|---|---|---|
| Data collection | | |
| Space group | P 21 21 21 | P 21 21 21 |
| Cell dimensions | | |
| a, b, c (Å) | 36.19 73.07 116.54 | 36.050, 72.751, 116.390 |
| α, β. γ (°) | 90.00, 90.00, 90.00 | 90.00, 90.00, 90.00 |
| Resolution (Å) | 73.07-1.77 | 73.07-1.77 |
| $R_{merge}$ | 0.109 (0.286) | 0.106 (0.206) |
| I/σI | 10.7 (2.4) | 12.7 (5.2) |
| Completeness (%) | 88.7 (48.2) | 98.6 (90 2) |
| Redundancy | 5.5 (1.7) | 6.4 (3.9) |
| Refinement | | |
| Resolution (Å) | 61.908-2.000 | 61.691-1.900 |
| No. reflections | 21321 | 23898 |
| $R_{work}/R_{free}$ | 0.1823/0.2165 | 0.1827/0.2277 |
| No. atoms | | |
| Protein | 2201 | 2196 |
| Ligand/ion | 1 | 35 |
| Water | 235 | 212 |
| B-Factors | | |
| Protein | 25.433 | 34.032 |
| Ligand/ion | 24.770 | 34.035 |
| Water | 31.275 | 39.342 |
| R.m.s. deviations | | |
| Bond lengths (Å) | 0.007 | 0.012 |
| Bond angles (°) | 0.820 | 1.094 |

Figure 3A:
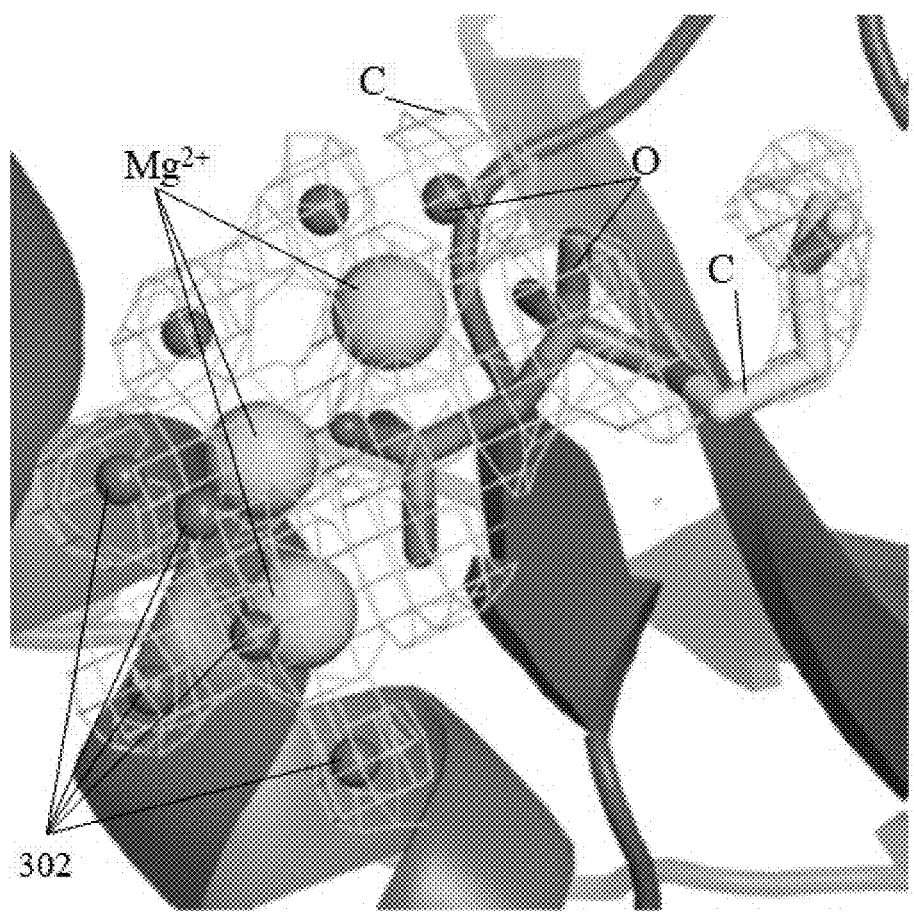
FIGS. 3A-3C show crystal structures of active site electron density maps of the following at pH 5.0: (1) IPP— and $Mg^{2+}$-bound AtNudx1 (FIG. 3A), showing unbiased Fo-Fc electron density omit map at contour level 2σ for IPP, active site $Mg^{2+}$ and coordinating waters 302; (2) $Mg^{2+}$ and phosphate coordination scheme in wild-type AtNudx1-IPP (FIG. 3B), with side chains of key residues shown as well; and (3) GPP-bound E56A mutant of AtNudx1 (pdb 5GP0) (FIG. 3C), with side chains of key residues shown in FIG. 3B shown in FIG. 3C as well for comparison.

As shown in Table 2, AtNudx1 crystallized without ligands (2.0 Å, $R_{work}$=0.1823 and $R_{free}$=0.2165) and with IPP bound (1.90 Å, $R_{work}$=0.1827 and $R_{free}$=0.2277). Now referring to FIG. 3A, models of IPP (pdb ligand ID IPR) and three magnesium cations (Mg$^{2+}$) are shown in active site electron density maps. IPP is clearly present in the active site of AtNudx1 (instead of the reaction product IP), which is likely due to the low pHs (pH 5.0) and low temperatures used during crystallization and data collection: 4° C. and −273° C., respectively. As shown in subpart 1 of FIG. 2B, at pH 6.5 the specific activity of AtNudx1 using IPP as a substrate is 7-fold lower than activities measured at the optimal pH of 8.5 (at 37° C.).

Like most Nudix superfamily members, AtNudx1 employs divalent cations for catalytic activity and, here, Mg$^{2+}$ ions were present in the crystallization conditions. As supported by the crystal structures shown in FIG. 3B, Mg$^{2+}$ octahedrally coordinates several water molecules 302, the sidechains of Glu56 (E56) and Glu60 (E60), the carbonyl oxygen of Gly40 (G40), and the diphosphate oxygens of IPP. The multivalent diphosphate group is also hydrogen bonded by His42 (H42) and Arg27 (R27). As shown in subpart a of FIG. 4, the C5 carbon chain of IPP is sequestered by the hydrophobic side chains of Ala11 (A11), Val12 (V12), Val13 (V13), Ile31 (I31), Ala37 (A37), Leu38 (L38), Phe78 (F78), Phe127 (F127), Pro129 (P129), Leu130 (L130), and Leu133 (not labeled).

Figure 3B:
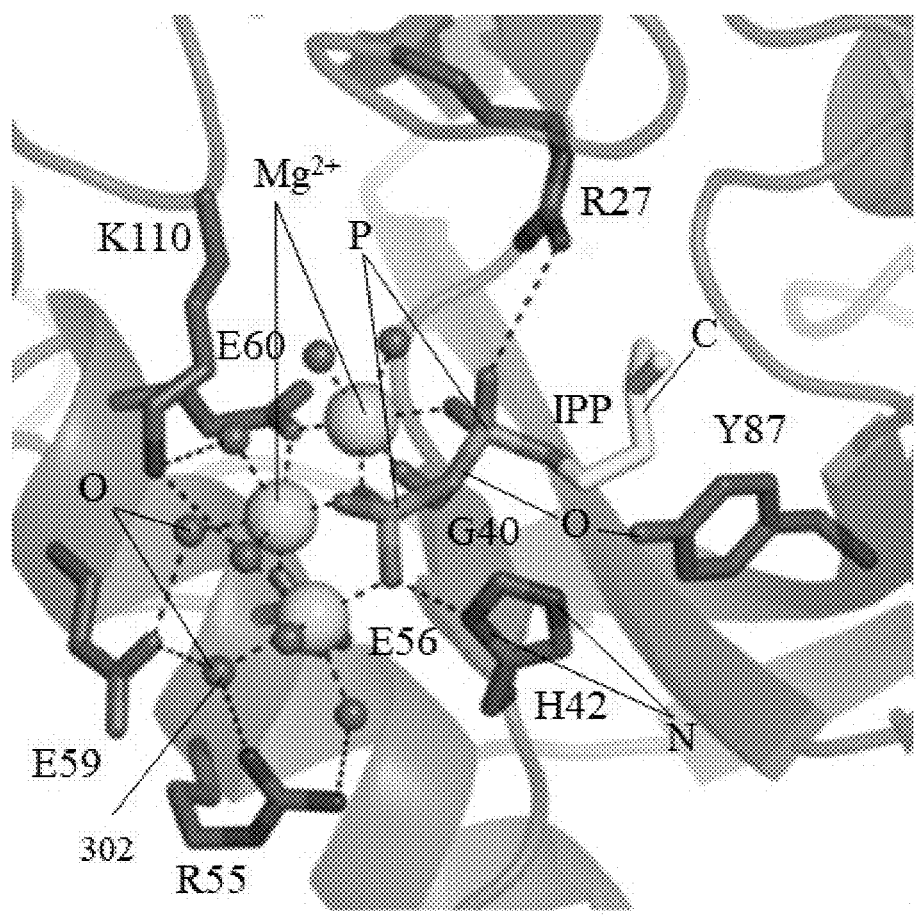
Figure 3C:
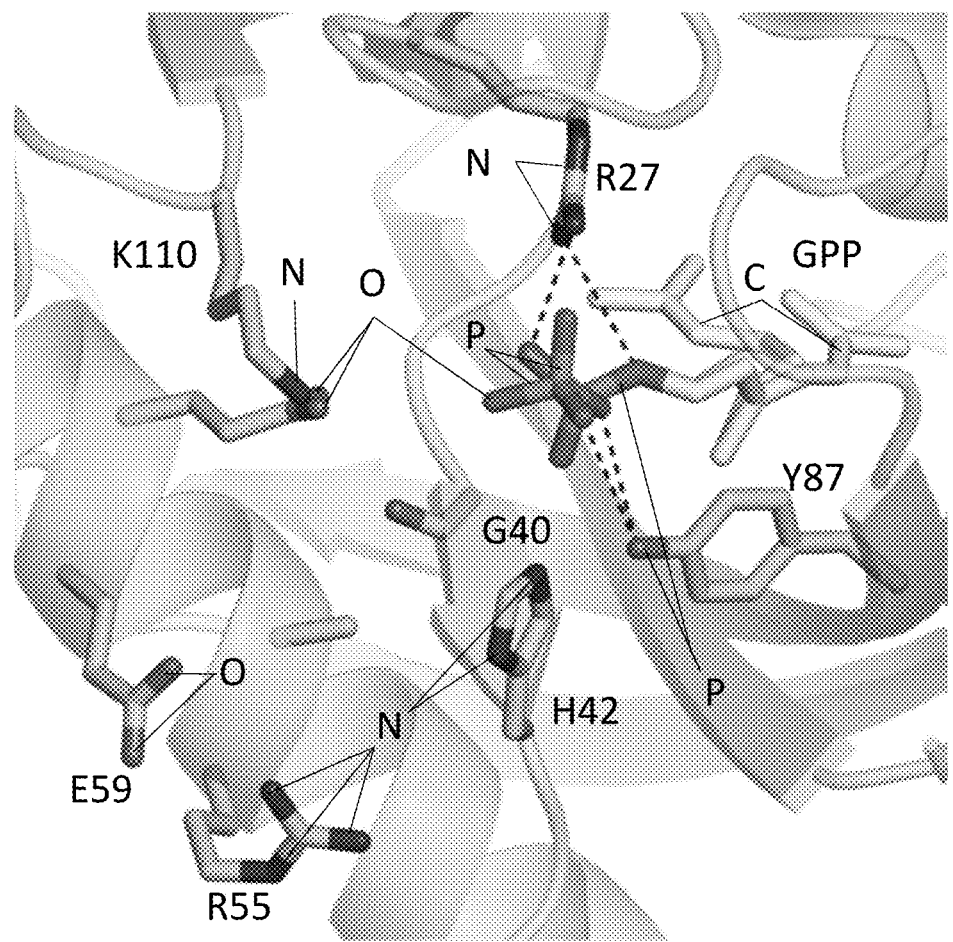

Recently, apo and GPP-bound E56A mutant structures of AtNudx1 have been reported. The apo structures (pdb 5WWD) and IPP— and GPP-bound structures (pdb 5GP0) superimposed with root mean squared deviations of 0.2969 Å and 0.3246 Å, respectively. Surprisingly, as shown in FIGS. 3B and 3C, superposition of the previously reported catalytically impaired AtNudx1 mutant (E56A) with GPP-bound (pdb 5GP0) (FIG. 3C) and the AtNudx1-IPP structure reported herein (FIG. 3B) show that the shared chemical features of these two ligands do not superimpose. Instead, the E56A mutation likely prevents $Mg^{2+}$ and GPP from binding in productive conformations.

In at least one the AtNudx1-IPP structure of the present disclosure shown in FIG. 3B, Glu56 bicoordinates with two of the active site $Mg^{2+}$ ions. $Mg^{2+}$ ions are absent in apo-AtNudx/of FIG. 3C, due to the absence of the diphosphate group which likely initiates cation recognition and early stages of divalent cation, active site coordination.

Figure 4:
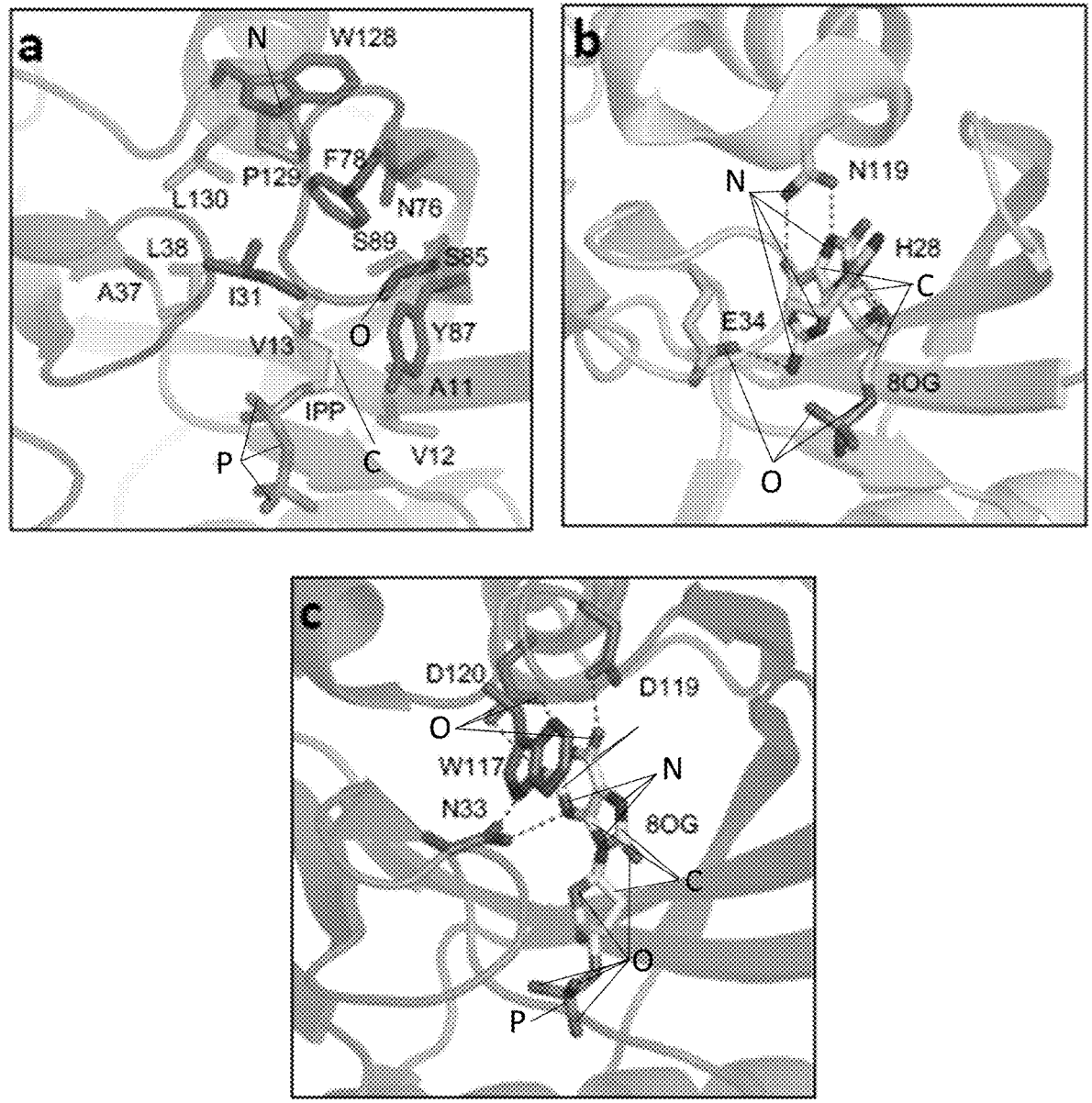
FIG. 4 demonstrates substrate recognition by *A. thaliana* Nudx1 and *E. coli* and human 8-oxo-dGTPase as displayed using crystal structures, with subpart a of FIG. 4 showing AtNudx1 with IPP bound (residue sidechains lining the active site pocket shown and $Mg^{2+}$ and phosphate interacting residues omitted for clarity), subpart b of FIG. 4 showing *E. coli* 8-oxo-dGTPase from with 8-oxo-dGMP (80G) bound (pdb 3A6T), and subpart c of FIG. 4 showing human 8-oxo-dGTPase with 8-oxo-dGMP bound (pdb 3ZR0) (side chains of key residues involved in the nucleotide binding shown)

To compare the chemical features governing substrate binding in these Nudix enzymes, the AtNudx1-IPP complex was structurally aligned with both 8-oxo-dGMP-bound *E. coli* 8-oxo-dGTPase MutT (pdb 3A6U) (see subpart b of FIG. 4) and human 8-oxo-GTPase MTH1 (pdb 3ZR0) (see subpart c of FIG. 4). Noticeably, as shown in subpart a of FIG. 4, residues that are important for binding the nucleotide substrate are absent in AtNudx1 (Glu34 (E34), His28 (H28), and Asn119 (N119) in MutT and Asn33 (N33), Asp119 (D119), Asp120 (D120), and Trp117 (W117) in MTH1).

Accordingly, despite sharing the same fold, AtNudx1 and 8-oxo-dGTPases possess distinct active site pockets for substrate recognition and catalysis. This, combined with in vitro substrate specificity studies described above, support that AtNudx1 activity with 8-oxo-dGTP is likely inconsequential in vivo.

Example 3

AtNudx1 and AtNudx3 Contribute to IP, and Possibly DMAP, Formation in Planta

Now referring to FIGS. 5A-5F, the in planta contribution of AtNudx1 and AtNudx3 to isoprenoid production was also investigated. Primarily, AtNudx1 and AtNudx3 expression across different tissues was analyzed using quantitative RT-PCR (qRT-PCR) with gene specific primers. For transient overexpression constructs, ORFs of AtNudx1 (G50379) and AtNudx3 (U16680) were obtained from the *Arabidopsis* Biological Resource Center and transferred from a Gateway-compatible entry vector into the binary vector pB2GW7 under the control of the cauliflower mosaic virus 35S promoter using the Gateway LR Clonase II (Invitrogen). Transient overexpression was achieved by *A. tumefaciens* (strain EHA105 carrying the corresponding construct) infiltration of 2-3 leaves of wild-type. Twenty-four hours after infiltration, scent emission was analyzed.

Further, RNA isolation from *Arabidopsis* and tobacco tissues, cDNA synthesis and qRT-PCR analysis were performed as described in Henry et al., Orthologs of the archaeal isopentenyl phosphate kinase regulate terpenoid production in plants, *Proc. Natl Acad. Sci. USA* 112, 10050-10055 (2015) (the "IPK Article"), the entirety of which is incorporated herein by reference. Gene-specific primers were designed using the PrimerExpress software (Applied Biosystems). For the absolute quantification of gene transcript levels, respective cDNA fragments were purified, diluted to several concentrations between 160 pg $ml^{-1}$ and 1.28 pg $ml^{-1}$, and used to generate standards curves in qRT-PCR with gene-specific primers. Absolute quantities of the individual transcripts were calculated on the basis of standard curves, and expressed as a pictograms (pg) of mRNA per 200 ng of total RNA or as a percentage of the expression in wild-type. Each data point represents three biological and three technical replicates.

Additionally, AtNudx1 promoter-GUS and AtNudx3 promoter-GUS reporter gene expression patterns were analyzed in mature flowers (each construct in 3 independent transgenic lines, all of which showed similar results, and floral and leaf volatiles collected using a closed-loop stripping system as is known in the art and described in the IPK Article). Approximately 2-kb regions upstream of each AtNudx1 and AtNudx3 genes were cloned from *Arabidopsis* Col-0 genomic DNA with primers containing attB Gateway linkers (pNDX1_F and pNDX1_R2; pNDX3_F and pNDX3_R2). The PCR products were inserted into the pDONR207 entry vector via a BP clonase I Gateway reaction (Invitrogen) and the fragment was sequenced to verify the identity of the insert. The insert was then moved from the pDONR207 entry vector into a pMDC163 expression vector (GUS expression vector) by LR clonase I Gateway reaction (Invitrogen). This expression vector was then transformed into *Agrobacterium tumefaciens* GV3101n and used for infiltration of *A. thaliana* Col-0 plants via the floral dip method. Hygromycin-resistant transformants were selected for GUS colorimetric assays.

Figure 6:
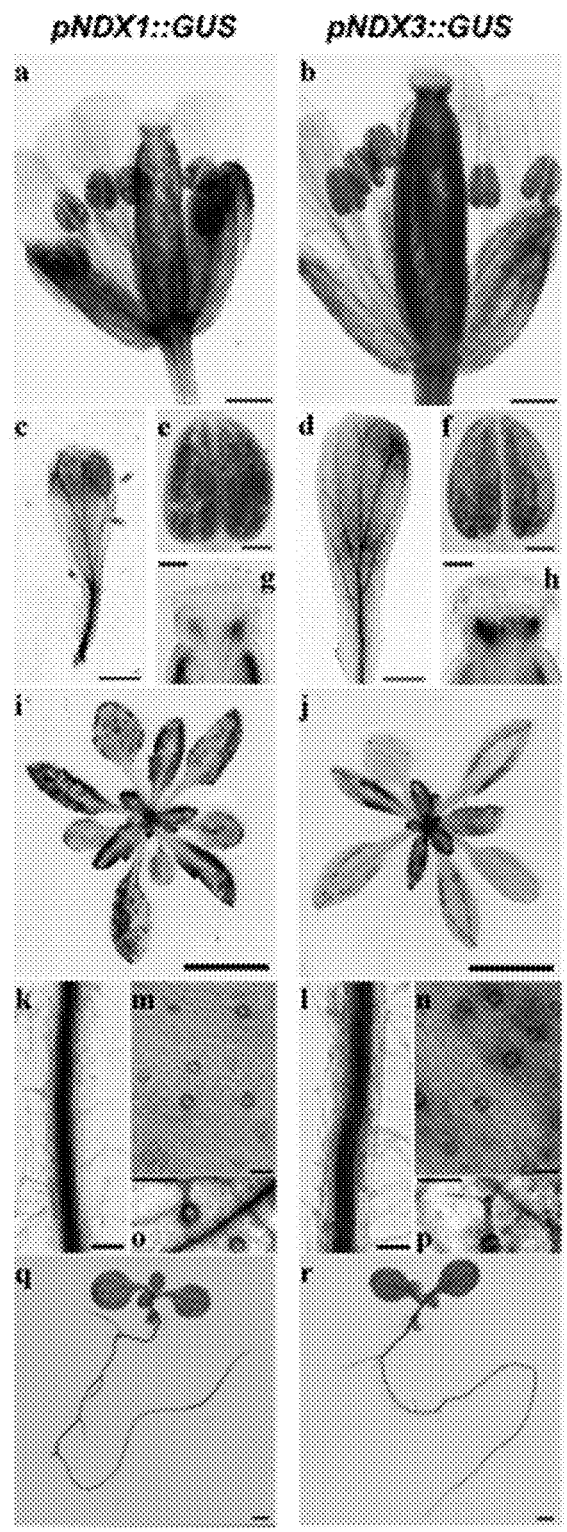
FIG. 6, subparts a-r, show tissue-specific expression of AtNudx1 and AtNudx3 (prepared using gene-type promoters fused to β-glucuronidase (GUS) reporter, the expression of which was verified using GUS staining solution), with AtNudx1 promoter-GUS shown in subparts a, c, e, g, i, k, m, o, and q, and AtNudx3 promoter-GUS shown in subparts b, d, f, h, j, 1, n, p, and r, and reporter gene expression patterns in mature flowers (subparts a and b), petals (subparts c and d), anthers (subparts e and f), stigmas and styles (subparts g and h), whole rosettes (subparts i and j), roots (subparts k and 1), guard cells (subparts m and n), trichomes (subparts o and p), and 7-day old seedlings (subparts q and r) (scale bars: 100 μm for subparts e, f, g, h, k, l, m, n, o, and p); 500 μm for subparts a, b, c, d, q, and r; and 3 cm for subparts i and j)

Tissues were then fixed in 90% acetone for 40 minutes at −20° C., washed twice with phosphate buffer (pH 7.0), added to GUS staining solution (0.1% Triton X-100, 10 mM EDTA, 2 mM ferricyanide, 100 mM sodium dibasic phosphate, 100 mM sodium monobasic phosphate and 4 mM 5-bromo-4-chloro-3-indolyl-β-glucuronide), vacuum-infiltrated for 5 minutes and incubated at 37° C. until staining was visible or for a maximum of 4 days. Tissues were then cleared in 70% ethanol for 2 days and thereafter imaged in a 8:2:1 chloral hydrate/distilled water/glycerol solution. The images of FIG. 6 were taken on a Nikon Eclipse Ti-2 inverted microscope with a Nikon Digital Sight DS-Fi2 camera and expression patterns were analyzed for each construct in at least three independent transgenic lines to account for positional effects of the insert.

Figure 5B:
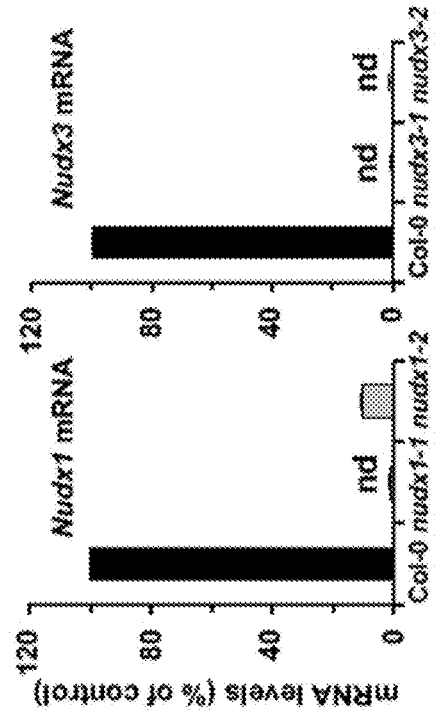
FIG. 5B shows a bar graph of the AtNudx1 and AtNudx3 transcript level data from Col-O and T-DNA insertion mutants determined by qRT-PCR.
Figure 5A:
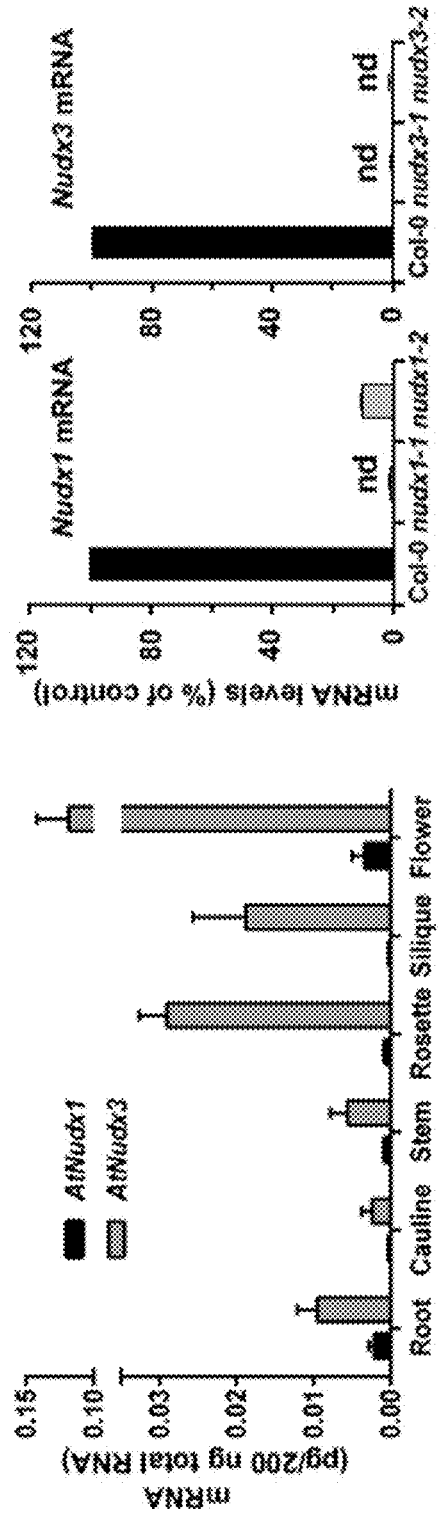
FIG. 5A shows a bar graph representative of AtNudx1 and AtNudx3 expression in various *Arabidopsis* tissues.

As shown in FIG. 5A, both Nudix genes expressed in all tissues with AtNudx3 mRNA at significantly higher levels than those of AtNudx1. In addition, expression of a β-glucuronidase (GUS) reporter under control of AtNudix1 and AtNudix3 promoters further indicates that their expression overlaps across different tissues (see FIG. 6).

Figure 7A:
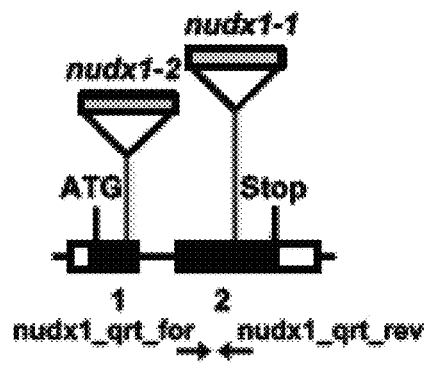
FIG. 7A shows the structure of the AtNudx1 green with two exons presented as filled and open 5' and 3' UTR boxes, with the arrows showing the positions of forward and reverse primers used for qRT-PCR analysis.
Figure 7B:
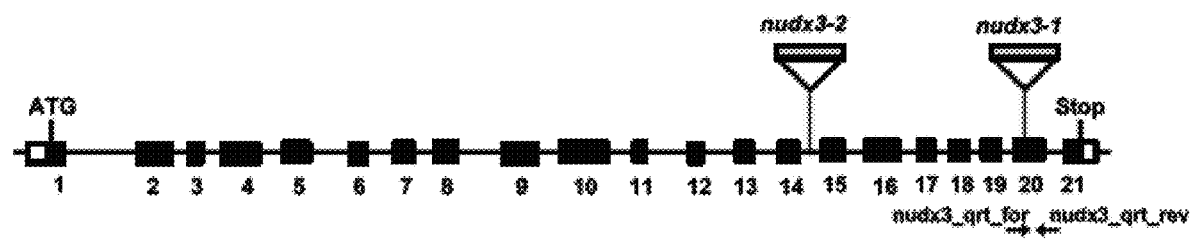
FIG. 7B shows the structure of the AtNudx3 gene with 21 exons presented as filled and opens 5' and 3' UTR boxes, with the arrows showing the positions of forward and reverse primers used for qRT-PCR analysis.

To further examine the role of AtNudx1 and AtNudx3, a reverse genetics approach was also utilized to profile terpenoids in *Arabidopsis* T-DNA insertion lines (nudx1-1, nudx1-2, nudx3-1 and nudx3-2). An AtNudx1 gene with the two exons presented as filled (coding region) and open 5' and 3' UTR boxes (see FIG. 7A) was used. In this examination, the T-DNA insertions (shown in gray) in the nud x1-1 and nudx1-2 mutants were located in exon 2 and exon 1, respectively. Further, the structure of the AtNudx3 gene is shown. Likewise, the AtNudx3 gene having 21 exons presented as filled (coding region) and open 5' and 3' UTR boxes was used. The T-DNA insertions, also shown in gray, in the nudx3-1 and nudx3-2 mutants were located in exon 20 and in the intron between exons 14 and 15, respectively.

Figure 5D:
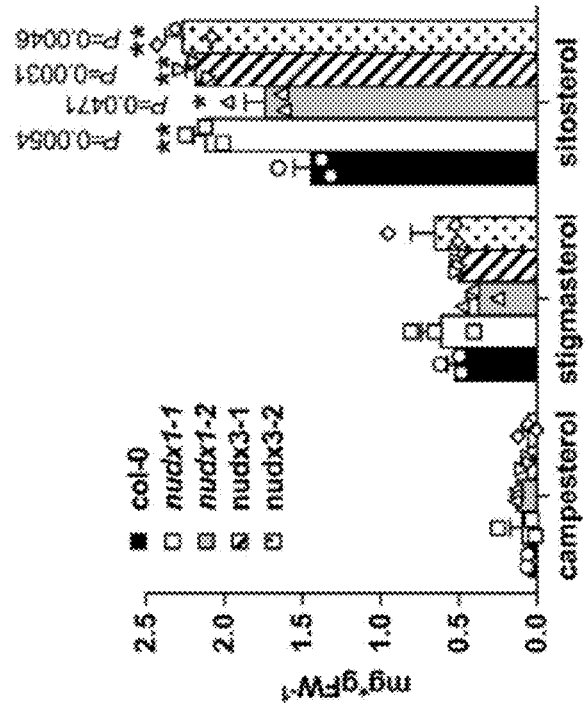
FIGS. 5C-5E show bar graphs representative of the effect of AtNudx1 and AtNudx3 knockouts on sterol and terpenoid formation, with β-Caryophyllene (FIG. 5C) and linalool (FIG. 5E) emission measured from flowers of 5-week-old *Arabidopsis* inflorescences, and sterol levels (FIG. 5D) measured in 8-day-old *Arabidopsis* seedlings of Col-O and nudx1 and nudx3 mutants.
Figure 5C:
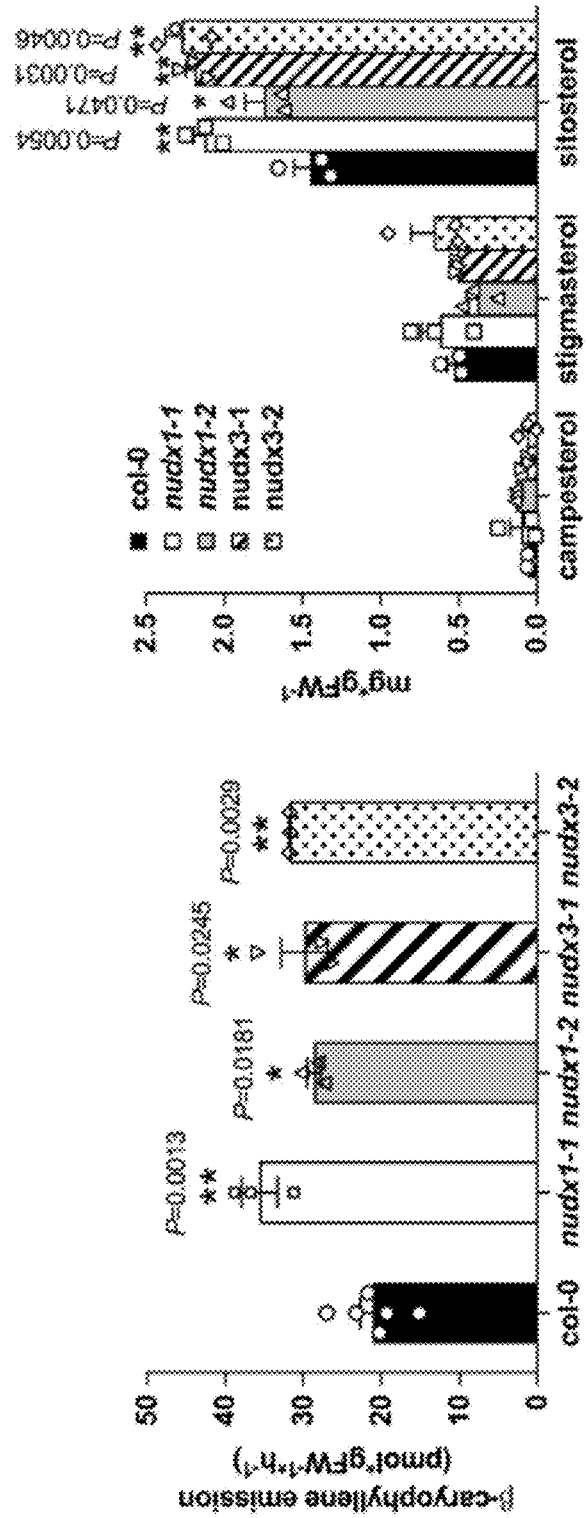

No AtNudx1 or AtNudx3 transcripts were detected in mutants with the exception of the nudx1-2 mutant, which, as shown in FIG. 5B, exhibited a 90% reduction in AtNudx1 expression. Significantly, emission of the most abundant sesquiterpene, β-caryophyllene, from *Arabidopsis* flowers increased by 28-60% (FIG. 5C) and the concentration of the sterol sitosterol nearly doubled in all nudx mutants, while the levels of campesterol and stigmasterol remained unchanged (FIG. 5D). Emission of the monoterpene linalool from flowers was increased 148-503% in all nudx T-DNA mutants (FIG. 5E), supporting that AtNudx1 and AtNudx3 modulate the ratios of IPP to IP and possibly DMAPP to DMAP in vivo.

Despite their differential expression levels (see FIG. 5A), the similar terpenoid metabolic profiles in the nudx1 and nudx3 mutants support that both AtNudx1 and AtNudx3 regulate the availability of metabolites contributing to both GPP- and FPP-derived terpenoids. As AtNudx1 and AtNudx3 are localized in the cytoplasm, it is probable that the observed effects on sterol levels and sesquiterpene emission result from dephosphorylation of IPP and/or FPP (see Table 1 and FIG. 1A). In contrast, because monoterpene formation partially relies on IPP imported into plastids from the cytoplasm, the observed effects on monoterpene levels can only result from IPP dephosphorylation.

Figure 8:
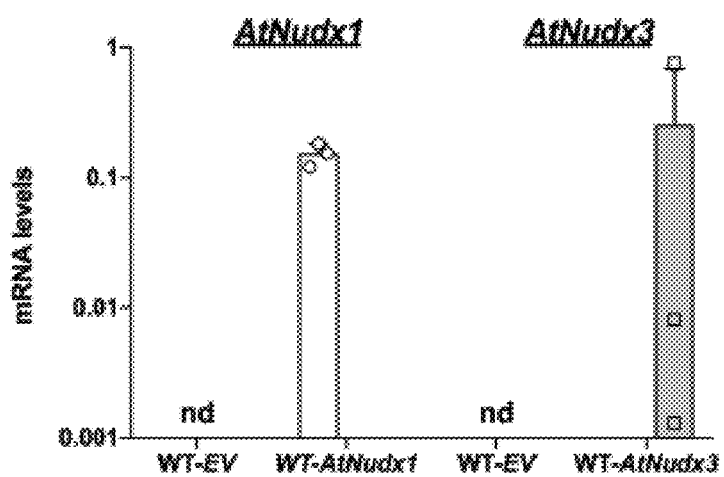
FIG. 8 shows a bar graph representative of levels of expression of AtNudx1 and AtNudx3 mRNAs in wild-type tobacco leaves that were infiltrated with *agrobacterium* carrying an empty vector control (EV), an AtNudx1 construct and an AtNudx3 construct, where absolute transcript levels of AtNudx1 (white bar) and AtNudx3 (gray bar) are shown as pg/200 ng total RNA (means±s.e.m., n=3 biologically independent samples)

Next, each Nudx gene was transiently overexpressed in wild-type *N. tabacum* (tobacco) leaves, which emit both monoterpene and sesquiterpene compounds. More specifically, tobacco leaves were infiltrated with *agrobacterium* carrying the empty vector control (EV) or an overexpression construct of AtNudx1 or AtNudx3 under the control of a CaMV-35S promoter (see FIG. 8 for result verification). Twenty-four hours after infiltration, the emission of sesquiterpenes in leaves overexpressing a Nudx gene was decreased by 57-88%, as compared to leaves infiltrated with *Agrobacteria* harboring an empty-vector (see FIG. 5*f*).

Figure 5F:
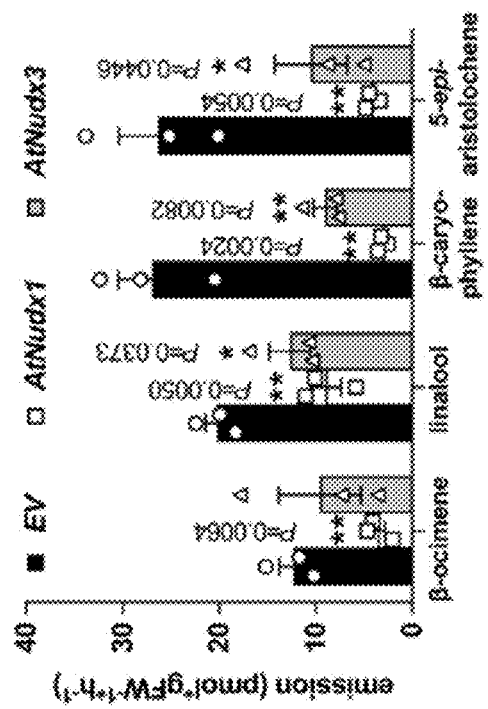
FIG. 5F shows a bar graph displaying data relative to the transient overexpression of AtNudx1 and AtNudx3 under control of a CaMV-35S promoter in tobacco leaves according to at least one embodiment of the present disclosure; wherein, all data displayed in FIGS. 5A-5F are means±s.e.m., n=3 biological independent samples, except (1) n=6 biological independent samples for Col-O in the data shown in FIGS. 5C and 5E, (2) *P<0.05; P 0.01; **P=0.0001 (two-tailed Student's t-test); (3) FW, fresh weight; and (4) nd, not detected.
Figure 5E:
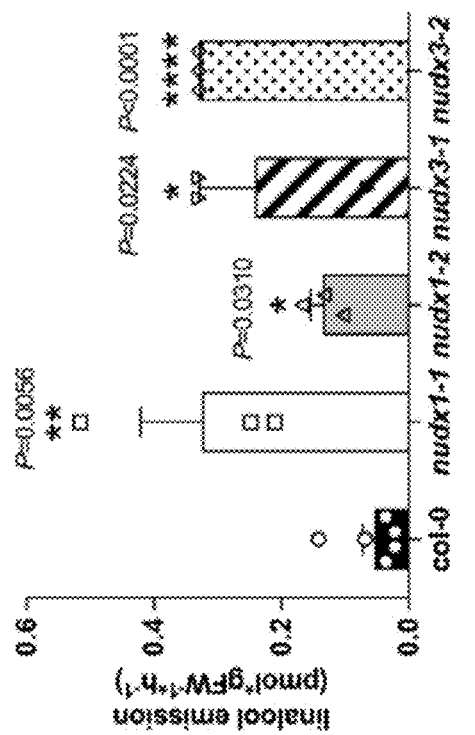

Emission of the monoterpenes linalool and β-ocimene also decreased on average by 50% in tobacco leaves overexpressing AtNudx1 and was lower, albeit not significantly, in tobacco leaves overexpressing AtNudx3 relative to control (FIG. 5*f*). Thus, overexpression of AtNudx1 and AtNudx3 resulted in an opposite metabolic phenotype to that observed when AtIPK was overexpressed in tobacco leaves. (see the IPK Article). When taken together, the *Arabidopsis* nudx1 and nudx3 mutants profiled in the present disclosure (FIGS. 5A-5F) and the ipk mutants analyzed previously produce observable complimentary phenotypes, which provides in vivo evidence that Nudix and IPK catalyze opposing reactions to regulate IPP/IP and possibly DMAPP/DMAP ratios.

Thus, in plant cells, IP and DMAP formation is not the consequence of dephosphorylation by non-specific phosphatases, but instead the result of the catalytic activity of specific Nudix enzymes. Moreover, because AtNudx1 and AtNudx3 dephosphorylate FPP (Table 1), the possibility that these enzymes also function to modulate the FPP to FP ratio cannot be excluded.

Accordingly, the data presented herein shows that the Nudix hydrolases function as a part of the key regulatory machinery that is capable of modulating the metabolic outcome of terpenoid metabolic networks in plants. Furthermore, the data presented herein demonstrates that IP and possibly DMAP in plants are not produced de novo, nor the result of cumulative effects of nonspecific phosphatase activity. Instead, IP (and possibly DMAP) originate from the active dephosphorylation of IPP (DMAPP) by dedicated Nudix hydrolases that regulate the concentration of the IPP.

Example 4

Effects of Increasing IP Formation on Terpenoid Biosynthesis

Pursuant to the above-described findings, it was determined that IP/DMAP is formed from the dedicated dephosphorylation of IPP/DMAPP catalyzed by Nudix superfamily hydrolases (FIGS. 5A-5F). Considering the limitations of the MVA pathway 100*a* for high yield terpenoid production, it was then tested if introducing de novo IP production in plants would affect flux toward downstream terpenoids.

As plants lack genes encoding MPDs, a bacterial MPD gene from *Roseiflexus castenholzii* (Rc) was used to encode an enzyme that possesses strict specificity for the efficient decarboxylation of MVAP to IP. To produce de novo IP, the overexpression MPD constructs were prepared pursuant to the methodologies described in connection with the AtNudx1 and AtNudx3 studies herein, and overexpression was achieved in tobacco plants as described herein or as otherwise known in the art.

The RcMPD gene was stably overexpressed in *N. tabacum* under control of the CaMV-35S promoter to create a bifurcation in the canonical MVA pathway 100 and, thus, produce IP without dephosphorylating IPP. It was thought that because the endogenous IPK is capable of converting MPD-generated IP to IPP, then RcMPD overexpression may result in the introduction of a novel second branch of the MVA pathway resembling the alternative MVA pathway 100*b* known to exist in some bacteria and archaea (FIG. 1B).

To generate transgenic tobacco plants overexpressing RcMPD, a RcMPD ORF was codon-optimized for plant systems and synthesized by Clontech. It was subcloned using the Gateway LR Clonase II (Invitrogen) into the binary vector pB2GW7 under the control of the cauliflower mosaic virus 35S promoter. Transgenic tobacco plants were obtained via *Agrobacterium tumefaciens* (strain EHA 105 carrying 35 S-RcMPD) leaf disc transformation using a standard transformation protocol. Plants rooted on BASTA selection (1 mgl-1) were screened for the RcMPD presence using forward and reverse, RcMPD_qRT_for and RcMPD_qRT_rev, primers. Untransformed tobacco plants as well as plants transformed with empty vector (EV) were used as controls in all experiments.

Figure 9A:
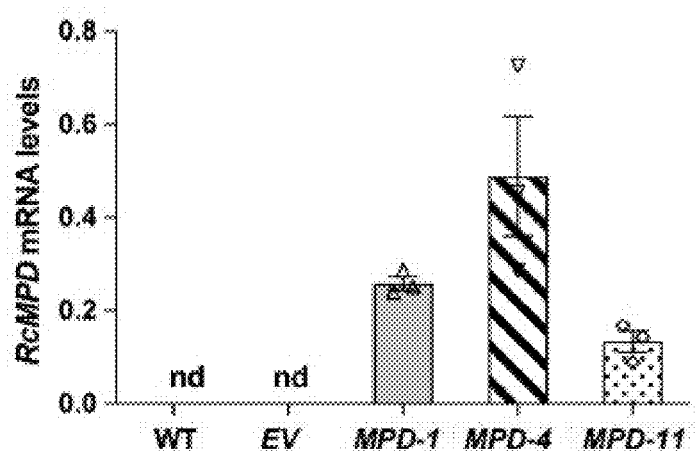
FIGS. 9A-9C display graphical data relating to the effect of *Roseiflexus castenholzii* MPD overexpression on terpenoid formation in tobacco, with FIG. 9A representative of the RcMPD transcript levels, determined by qRT-PCR, in wild-type and transgenic tobacco lines prepared pursuant to the present disclosure (empty vector control EV, MPD-1, MPD-4, and MPD-11), FIG. 9B representative of sterol levels in tobacco leaves of wild-type, EV control-, and RcMPD-overexpressing lines prepared pursuant to the current disclosure (data are means±s.e.m., n=5 biologically independent samples for WT and MPD-11, n=3 biological independent samples for EV, and n=6 biologically independent samples for MPD-1 and MPD-4), and FIG. 9C representative of emission of monoterpenes, β-caryophyllene and 5-epi-aristolochene, from tobacco leaves of wild-type, EV control- and RcMPD-overexpressing lines prepared pursuant to the present disclosure (data are means±s.e.m., n=6 biologically independent samples for WT, except n=3 biologically independent samples for EV and MPD-11, n=5 biologically independent samples for MPD-1, and n=8 biologically independent samples for and MPD-4); *P<0.05; P<0.01; *P=0.001 (two-tailed Student's t-test); nd=not detected.
Figure 9B:
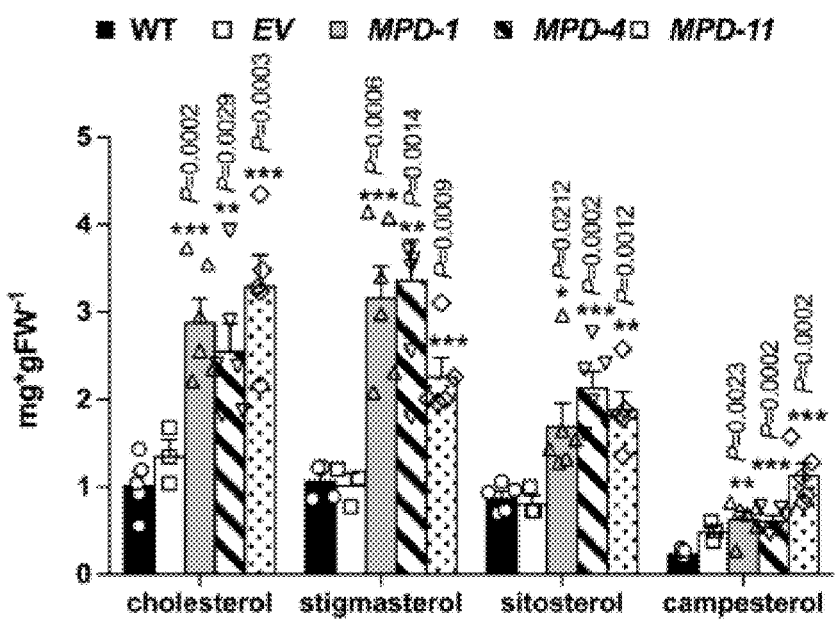
Figure 9C:
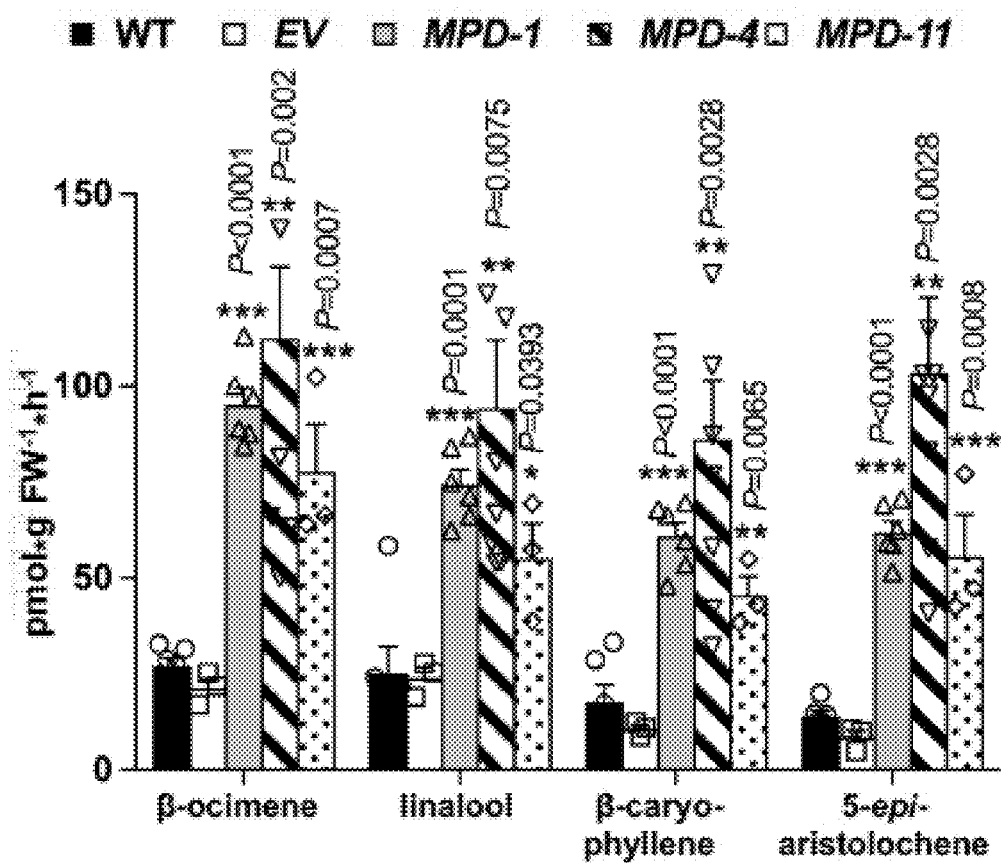
Figure 10A:
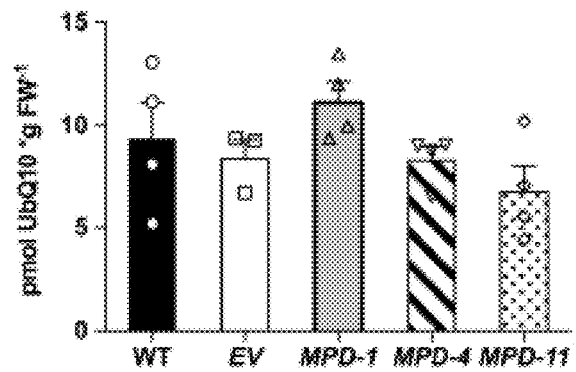
FIGS. 10A-10E display graphical data from the analysis of terpenoid-quinone conjugates in tobacco leaves of wild-type, EV control, and RcMPD overexpressing lines, with FIG. 10A representative of the amount of the MVA 100-derived terpenoid-quinone conjugate, ubiquinone in each sample and FIGS. 10B-10E representative of the amounts of MEP-pathway 102 derived terpenoid-quinone conjugates in each sample including plastoquinone (FIG. 10B), α- and γ-tocopherols (FIGS. 10C and 10D, respectively), and phylloquinone (FIG. 10E) (data are means±s.e.m., n=4 biologically independent samples, except for EV in FIG. 10A and RcMPD-11 in FIG. 10D, which are n=3)
Figure 10B:
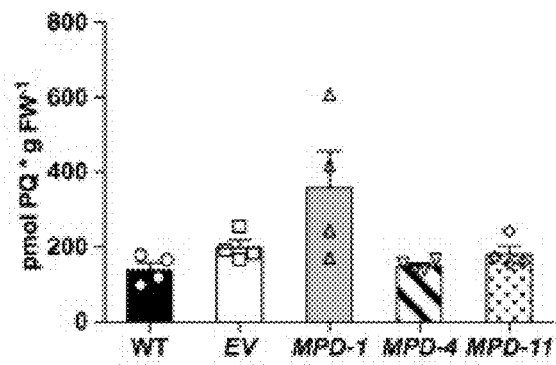
Figure 10C:
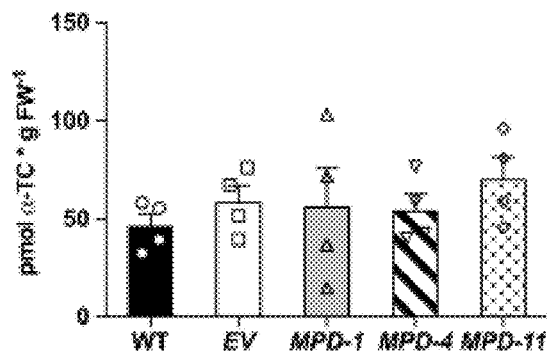
Figure 10D:
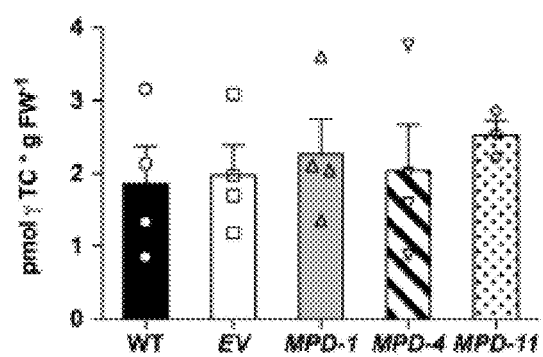
Figure 10E:
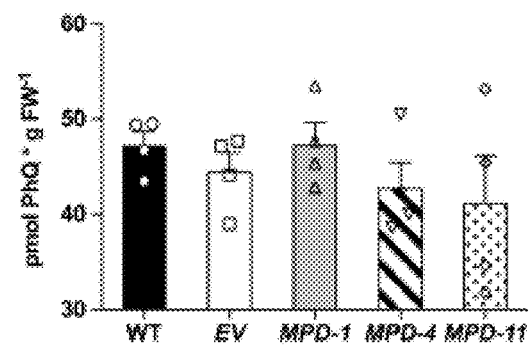

Metabolic analyses of three independent transgenic lines with different expression levels of the RcMPD gene, namely MPD-1, MPD-4, and MPD-11 (FIG. 9A), revealed that all lines exhibited a substantial increase in overall terpenoid production relative to wild-type and EV control plants without affecting expression of endogenous IPK, PMK and MDD. As shown in FIG. 9C, sterol levels, including cholesterol, stigmasterol, sitosterol, and campesterol were respectively 3.2-, 4.2-, 3.2- and 3.7-fold higher in RcMPD transgenic plants of the present disclosure relative to controls. (Sterol extraction and analysis were performed pursuant to methods commonly known in the art and as described in the IPK Article.)

As shown in FIGS. 10A-10E, while more elaborate downstream terpenoid-quinone conjugate products were not affected, this is likely due to limited availability of the aromatic building blocks necessary for their biosynthesis. Finally, as shown in FIG. 9C, the leaves of MPD transgenic plants of the present disclosure emitted up to 4.1- and 7.4-fold more mono- and sesquiterpenes, respectively, than control plants.

The increased production of terpenoids in RcMPD overexpression lines indicates that endogenous IPK can access and process de novo-produced IP to IPP and that the upstream portion of the MVA pathway 100a provides sufficient MVAP substrate to measurably increase flux through the introduced alternative MVA pathway 100b. In comparison to previously generated AtIPK overexpression tobacco lines, the RcMPD transgenics of the present disclosure produced 1.5-fold more sterols and up to 2-fold higher levels of mono- and sesquiterpenes, thus supporting that overall yields of terpenoid products from both the MVA and MEP metabolic networks 100, 102 and crosstalk between the two are limited by endogenous IP levels and a firm basis for leveraging these transgenics to achieve increased terpenoid output.

Figure 11A:
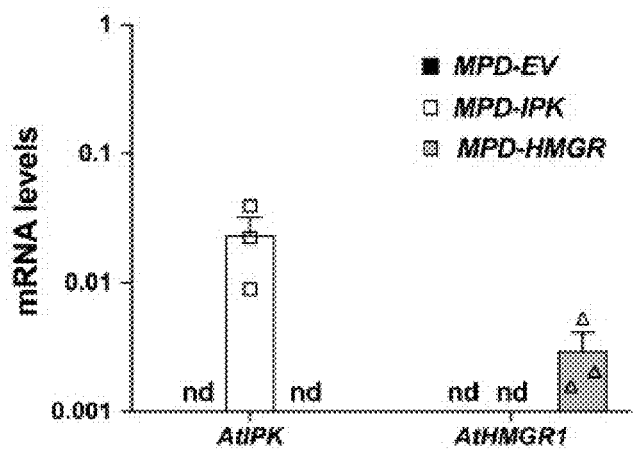
FIGS. 11A and 11B display graphical data representative of the effect of overexpression of AtIPK and AtHMGR1 on terpenoid formation in a RcMPD-4 tobacco transgenic line of the present disclosure, where
Figure 11B:
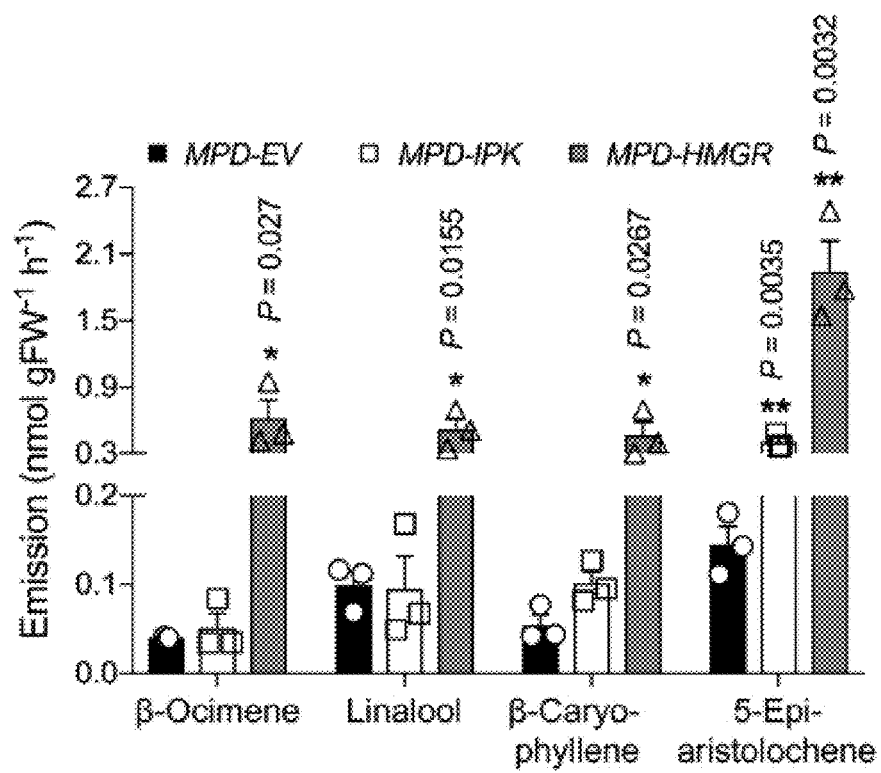

To assess whether endogenous IPK in MPD transgenic plants of the present disclosure depleted all de novo generated IP, in at least one trial AtIPK was transiently overexpressed in the MPD-4 transgenic line (employing the heterologous expression and purification methods previously described, except that IPK ORFS were codon-optimized for E. coli expression and synthesized by Integrated DNA Technologies). AtIPK overexpression in this background resulted in additional increases of 1.9- and 2.8-fold in emitted sesquiterpenes β-caryophyllene and 5-epi-aristolochene, respectively, relative to the levels in the MPD-4 transgenic line overexpressing an empty vector (FIG. 11B).

These results support that endogenous IPK activity was limiting in the MPD transgenics. Moreover, while sesquiterpene levels increased, levels of the emitted monoterpenes (β-ocimene and linalool) remained unchanged. This effect on the MEP-pathway 102 derived terpenoids may be caused by the IPP transporter (involved in importing cytoplasmic IPP into plastids, and/or plastidial enzymes acting downstream of IPP) working at maximum capacity in these plant backgrounds and/or the occurrence of an increased flux toward sesquiterpene formation due to the turnover of IP by IPK to relax FPP synthase inhibition, as IP and DMAP competitively inhibited FPP synthase.

Example 5

Overexpression of HMGR and MPD Significantly Amplifies Flux Toward Downstream Products It is conventionally thought that HMGR catalyzes the rate-limiting step of the MVA pathway 100a. To test whether increasing expression of HMGR in the RcMPD background further enhances terpenoid production, AtHMGR (G12571) was transiently overexpressed in RcMPD transgenic tobacco leaves (using methods previously described). The transient overexpression constructs were prepared as previously described in connection with the AtNudx1 and AtNudx3 studies herein, except that for the santalene synthase overexpression constructs, full-length SaSSy was also subcloned into the binary vector pB2GW7. Transient overexpression was achieved by A. tumefaciens (strain EHA105 carrying the corresponding construct) infiltration of 203 leaves of wild-type or RcMPD-4 transgenic tobacco plants as described herein or as otherwise known in the art. Further, for plants co-infiltrated with multiple constructs, equal amounts of Agrobacterium cultures with $OD_{600\ nm}$ 1.0 were mixed and infiltrated.

As supported by FIG. 11B, compared to the MPD-4 line expressing an empty-vector as a control, levels of the monoterpenes β-ocimene and linalool increased by 2.7- and 4.6-fold, respectively, in MPD-4 lines also overexpressing AtHMGR. Even higher levels were achieved for the sesquiterpenes β-caryophyllene and 5-epi-aristolochene, reaching 4.6- and 16.5-fold increases, respectively. When taken with the findings previously discussed herein, the coexpression of AtHMGR with RcMPD in tobacco leaves enhances monoterpene formation by up to 20-fold and sesquiterpene production by up to or greater than 130-fold relative to their production in wild type plants (see FIGS. 9C and 11B), which is far greater than any production increase achieved to date using conventional methodologies.

To further investigate the suitability of the AtHMGR-RcMPD tobacco platform for heterologous production of valuable terpenoids (i.e. terpenoids that are non-native to the underlying plant), Santalum album santalene synthase (SaSSy) was also coexpressed. FIG. 12A illustrates levels of SaSSy and AtHMGR1 mRNAs in wild type and RcMPD-4 transgenic tobacco leaves infiltrated with Agrobacterium carrying (1) the SaSSy construct alone, and (2) the AtHMGR1 construct in combination with the SaSSy construct. As shown in FIGS. 12A and 12B, overexpression of SaSSy with both AtHMGR and RcMPD resulted in almost 10-fold higher emitted levels of the non-native sesquiterpenes α-exo-bergamotene and α-santalene as compared to overexpression of the SaSSy gene alone in wild type background. This data confirms that in addition to increasing production of terpenoids naturally produced by the underlying plant species, the inventive methods and platforms of the present disclosure can be employed to increase production of terpenoids that are non-native to the underlying plant (i.e. not naturally occurring therein but added through transformation or other techniques for achieving heterologous terpenoid production).

Example 6

PMK Contributes to Controlling Carbon Flux Through the MVA Pathway

The introduced bacterial RcMPD and endogenous NtPMK genes both encode enzymes that use MVAP as a substrate (see FIGS. 1A and 1B). While PMK in plants resides in peroxisomes, it is assumed that bacterial RcMPD localizes to the cytoplasm. In this scenario, the increase in terpenoid production observed in RcMPD transgenic lines may result from the introduction of an alternative biosynthetic route that bypasses the peroxisomal MVAP import and IPP export steps associated with the naturally-occurring plant MVA pathway 100a. To test this hypothesis, the in planta subcellular localization of the introduced RcMPD protein was examined.

GFP was fused to either the N-terminus or C-terminus of RcMPD and transiently expressed in Nicotiana benthamiana leaves. Briefly, the RcMPD ORF was cloned into the binary vectors pK7FWG2 and pK7WGF2 with and without stop codons to generate N- and C-terminal GFP-fusion constructs, respectively. mCherry markers for peroxisome (px-rk CD3-983) and mitochondria (mt-rk CD3-991) were co-infiltrated with GFP constructs pursuant to methodologies known in the art. Constructs, markers and EV controls were transformed into Agrobacterium (EHA105) and infiltrated into 3-week-old N. benthamiana leaves as previously described and pursuant to methods known in the art. Plant tissues were analyzed 1-2 days after infiltration using the Nikon A1Rsi laser scanning confocal microscope.

Figure 13:
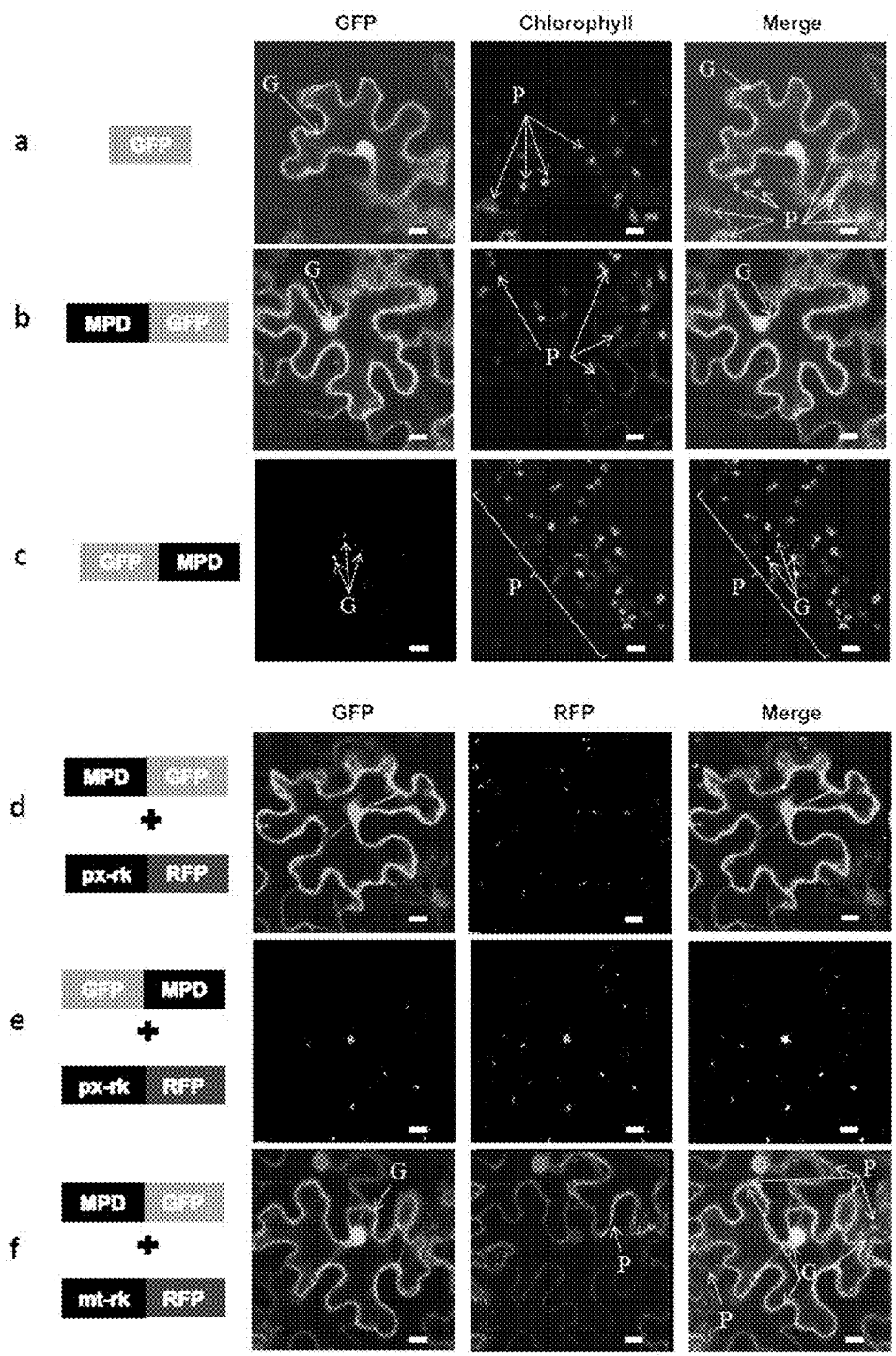
FIG. 13 illustrates, for each GFP fusion construct a-f, a schematic diagram on the left and the corresponding transient expression in *N. benthiamiana* leaves detected by confocal laser scanning microscopy shown on the right, with construct a: a transient overexpression of GFP empty vector control, construct b: a RcMPD fused to an N-terminal of GFP (MPD-GFP), construct c: RcMPD fused to a C-terminal GFP (GFP-MPD), with all GFP fluorescence and chlorophyll autofluorescence in constructs a-c shown in the left and middle panels, respectively, while the merged panels show the overlay of GFP and chlorophyll fluorescence (GFP alone and chlorophyll autofluorescence were used as cytosolic and plastidic markers, respectively); and constructs d-f showing coinfiltration of RcMPD GFP constructs with peroxisomal (px-rk) (constructs d and e) and mitochondrial (mt-rk) (construct e) markers, labeled with RFP and shown in the middle, with the merged panels showing the overlay of GFP and RFP fluorescence (these experiments were repeated independently three times with similar results; scale bar, 5 μm)

As shown in FIG. 13, the GFP signal for the C-terminal GFP fusion protein RcMDP-GFP was detected in the cytoplasm. In contrast and unexpectedly, the green fluorescence of GFP (labelled G) associated with N-terminal GFP fusion protein GFP-RcMPD was observed in peroxisomes (for reference, RFP is labelled P), which supports that the bacterial RcMPD possesses a cryptic peroxisomal targeting signal that is blocked upon fusion of GFP to RcMPD's C-terminus. Further, examination of the bacterial RcMPD sequence (see FIG. 13g) also revealed a peroxisomal targeting signal type 2 (PTS2 motifs labeled in box 1301; (R/K) (L/V/I) X5 (H/Q) (L/A) labelled box 1302) which, despite not being present in the N-terminus, was perhaps still recognized by the plant peroxisomal import machinery. While initially assumed the increase in terpenoid formation was due to bypass of the peroxisome, the above construct data negated that theory. Instead, it was determined that the RcMPD did in fact localize in the peroxisome and that substrate and transport out of peroxisomes are not limiting factors with respect to terpenoid synthesis.

Given RcMPD's peroxisomal localization, the enhanced terpenoid production in RcMPD- and MPD4-AtIPK tobacco transgenics shown herein indicates that generated IP can be transported out of this organelle (likely in a similar way as IPP). These results also support that peroxisomal MVAP levels are sufficient to achieve the observed increases in overall terpenoid production (see FIG. 11B). Therefore, flux through the classical MVA pathway 100a is, at least in part, limited by the conversion of MVAP to MVAPP by PMK (a heretofore unsuspected regulatory hub in the plant MVA pathway).

Figure 14A:
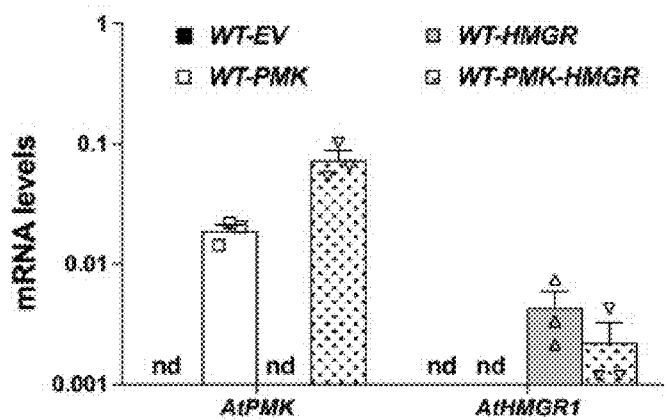
FIGS. 14A and 14B show graphical data regarding the effect of AtPMK and AtHMGR1 overexpression on terpenoid formation in transgenic tobacco leaves produced pursuant to the current disclosure, where
Figure 14B:
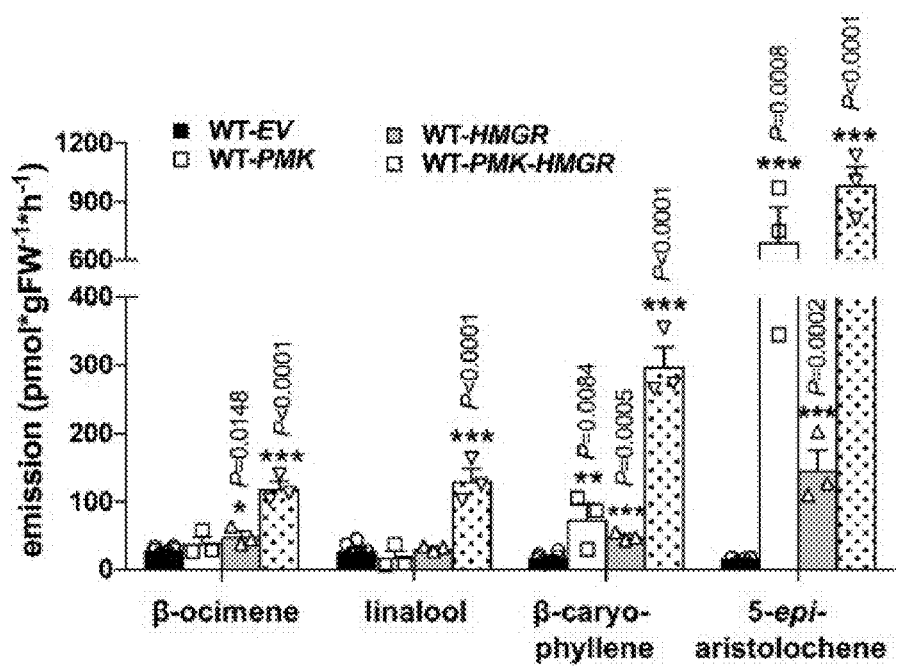

To further support this finding, Arabidopsis PMK was transiently overexpressed in wild-type tobacco leaves under control of the CaMV 35S promoter using the methodologies previously described (see FIG. 14A) (N. tabacum PMK ORF's were codon-optimized for E. coli expression and synthesized by SGI-DNA). As shown in FIG. 14B, relative to the empty-vector control, AtPMK overexpression led to 4- and 44-fold increases in β-caryophyllene and 5-epi-aristolochene levels, respectively, with negligible effects on monoterpene levels. Next, to catalyze the rate-limiting step of the MVA pathway 100a, AtHMGR was transiently coexpressed with AtPMK in wild-type tobacco leaves. For this study, AtHMGR was also transiently overexpressed alone (as compared to EV controls), which led to increased emission of sesquiterpenes (2.8- and 9.4-fold for β-caryophyllene and 5-epi-aristolochene, respectively), but no discernable effect on monoterpene levels.

Compared to overexpressing AtPMK and AtHMGR individually, the results shown in FIG. 14B clearly illustrate that overexpressing the two genes together further increased β-caryophyllene and 5-epi-aristolochene emission by 17- and 63-fold, respectively, relative to the EV control. Coexpressing AtPMK and AtHMGR also increased emission of monoterpenes by 4.6-fold (on average), which is indicative of sufficient IPP levels being produced in the cytoplasm to drive plastidial terpenoid biosynthesis.

These results demonstrate that PMK does indeed share control of flux with HMGR through the plant MVA pathway 100a and may in fact pull on the peroxisomal MVAP pool imported from the cytoplasm. This shift in the transport equilibrium toward peroxisomes depends on PMK catalytic efficiency and PMK's peroxisomal concentration. In contrast to all other enzymes of the classical MVA pathway 100a except MKs, PMKs are encoded by single copy genes. Previous biochemical characterization of Arabidopis PMK (AtPMK, At1g31910) as well as N. tabacum PMK (NtPMK, XP 016504246) described herein, shows that PMKs possess high specificity for MVAP with $K_M$ values of 12 μM[13] and 31 μM, respectively.

TABLE 3

| Kinetic parameters of N. tabacum PMK and IPK. | | | | | | |
|---|---|---|---|---|---|---|
| Organism | UniProt | Enzyme | Substrate | $K_M$ (μm) | $k_{cat}$ (s$^{-1}$) | $k_{cat}/K_M$ (M$^{-1}$ s$^{-1}$) |
| N. tabacum | A0A1S4CT09 | PMK | (R)-MVAP | 31 ± 7 | 22 ± 1 | 7.1 × 10$^5$ ± 1.6 |
| | A0A1S4BSB2 | IPK | IP | 4.0 ± 1.5 | 0.93 ± 0.05 | 2.3 × 10$^5$ ± 0.9 |
| | | | DMAP | 8.5 ± 2.3 | 1.20 ± 0.06 | 1.4 × 10$^5$ ± 0.4 |
| | | | GP | 100 ± 60 | 0.0017 ± 0.0002 | 1.7 × 10$^3$ ± 1 |

The catalytic efficiencies ($k_{cat}/K_M$) of PMKs from both species were comparable (1.7×10$^6$ and 7.1×10$^5$ M$^{-1}$s$^{-1}$ for AtPMK[13] and NtPMK, respectively). These efficiencies are also similar to AtIPK (1.0×10$^5$ M$^{-1}$s$^{-1}$) characterized previously and NtIPK (XP_009616074) (2.3×10$^5$ M$^{-1}$s$^{-1}$) and in Table 3. As PMK is catalytically efficient, and its encoding gene is one of the most highly expressed MVA pathway genes, unexplored transcriptional and/or posttranscriptional regulation may control PMK activity and metabolic flux through the MVA pathway 100a.

The unexpected, and heretofore unknown, peroxisomal localization of the overexpressed RcMPD, which competes with the same MVAP substrate as PMK, demonstrates that the MVAPP formed by PMK is likely a limiting factor for the biosynthesis of downstream MVA-derived terpenoids. Indeed, transient overexpression of AtPMK in wild-type tobacco led to some increase in emitted sesquiterpenes, as did overexpression of AtHMGR (FIG. 11B); however, coexpression of AtPMK and AtHMGR substantially enhanced the formation of both sesquiterpenes and monoterpenes relative to the EV controls. This supports that these two genes are positively epistatic and encode enzymes that have major roles in controlling flux through the plant MVA pathway 100a. When AtHMGR was coexpressed with RcMPD, the latter providing a bypass to the PMK-catalyzed reaction, again, synergistic effects were observed for both emitted sesquiterpenes and monoterpenes (FIG. 11B). These results further support PMK being an unsuspected regulatory hub in the plant MVA pathway 100a and suggest a role for IP in regulating the formation of both MVA and MEP pathway-derived terpenoids.

All enzyme assays described in the present disclosure were performed as follows. Phosphatase activity was monitored at 37° C. using BIOMOL Green reagent (Enzo Life Sciences) to detect and quantify released phosphate at 623 nm using a phosphate standard curve. The optimum pH for activity was determined using a three-component buffer system of 50 mM acetic acid, 50 mM IVIES, and 100 mM Tris-HCl with 0.1 mM IPP as substrate. Magnesium ion dependence was investigated with 1 mM to 20 mM $MgCl_2$. Steady-state parameters were determined in 100 mM TAPS pH 8.5 with 10 mM $MgCl_2$ and varied concentrations of substrates IPP, DMAPP, GPP, FPP, and 8-oxo-dGTP (Tri-Link Biotechnologies). Assays with 8-oxo-dGTP included 0.05 U of inorganic pyrophosphatase (ThermoFisher Scientific) per 0.1 ml assay. Reactions were initiated by the addition of enzyme and quenched by the addition of BIO-MOL Green.

Activities of the NtPMK and MIPK were analyzed by the lactate dehydrogenase/pyruvate kinase coupled assay as detailed in the IPK Article. Briefly, assays were conducted in 100 mM NatHepes pH 7.5 supplemented with 8 mM $MgCl_2$ and 100 mM KCl with coupling enzymes pyruvate kinase/lactate dehydrogenase (Sigma), 4 mM ATP, 2 mM phosphoenolpyruvate, 0.16 mM NADH and varied concentrations of (R)-MVAP (Sigma) and IP (isoprenoids) as substrate for NtPMK and MIPK, respectively. Reactions were monitored at 340 nm and 30° C. Controls included assays without enzyme and without substrate. All enzyme assays were performed at an appropriate enzyme concentration so that the reaction velocity was linear and proportional to the enzyme concentration during the incubation time period. Kinetic data was fitted using Prism (GraphPad Software) to the Michaelis-Menten equation to compute $K_M$ and $k_{cat}$. At least triplicate assays were performed for all data points.

Resulting Findings and Systems, Methods, and Platforms

The findings described herein can be leveraged to provide new strategies for high-level production of economically valuable terpenes and terpenoids. In at least one embodiment of the present disclosure, a transgenic plant comprises a first heterologous nucleic acid encoding a polypeptide having HMGR activity and a second heterologous nucleic acid encoding a second polypeptide. In at least one embodiment, the first and/or second heterologous nucleic acid(s) may be from *Arabidopsis*. The polypeptide encoded by the second heterologous nucleic acid may comprise a polypeptide that introduces de novo formation of IP in the transgenic plant or a polypeptide having PMK activity and, in such cases, the second heterologous nucleic acid may comprise a bacterial gene such as, without limitation, an MPD gene from *Roseiflexus castenholzii* (Rc). Such genes may be transiently or stably overexpressed depending on the desired application.

In at least one embodiment, one or both of the first and second heterologous nucleic acids are operably linked to a regulatory element for directing expression of such heterologous nucleic acid. For example, the regulatory element may comprise a promoter. In at least one embodiment, the promoter comprises a tissue-specific promoter to confer expression of the first or second heterologous nucleic acid molecule to specific plant tissue(s) or cells of the transgenic plant such as, for example, a leaf, root, flower, developing ovule, seeds, fruits, embryo, meristems, etc.

Where the polypeptide encoded by the second heterologous nucleic acid has MPD activity, the resulting transgenic plant exhibits increased activity of both HMGR and MPD and, when grown under the desired conditions, exhibits an increase in the metabolically available IP within the transgenic plant cells as a result of the overexpression of MPD. This provides a bypass to the PMK-catalyzed reaction and, in turn, results in a significant uptick in the production of endogenous terpenoids (at least a 20-100 fold increase) as compared to the terpenoid production capabilities of a wild-type plant or those transgenic plants prepared pursuant to conventional methodologies. Indeed, such coexpression of HMGR and MPD in the transgenic plant of the present disclosure can increase monoterpene formation by up to 20-fold and sesquiterpene production by up to or greater than 130-fold (both as compared to the production of such terpenoids in wild-type plants).

At least one of the reasons for this greatly enhanced increase in terpenoid production relates to the novel manipulation of both the MEP and MVA pathways. While the overexpression of HMGR manipulates the cytosolic MVA pathway 100a by increasing the metabolically available IP, overexpression of MPD as disclosed herein concurrently introduces de novo IP production in the transgenic plant. In comparison, transgenic plants of the prior art rely solely on the manipulation of the plastidial MEP pathway 102 and only see a marginal increase in terpenoid production of about 2-fold relative to wild-type.

Alternatively, where the second heterologous nucleic acid transgenic plant of the present disclosure has PMK activity such that both HMGR and PMK (*Arabidopsis* HMGR and/or PMK, for example) are overexpressed in the transgenic plant, PMK's peroxisomal concentration increases thus increasing flux through the classical MVA pathway 100a and driving plastidial terpenoid biosynthesis. As supported by the data of the present disclosure, the overexpression of HMGR and PMK together results in substantially enhanced formation of both sesquiterpenes and monoterpenes relative to EV controls (i.e. wild-type plant cells); at or near a 20-fold increase in production of endogenous monoterpenes and at or near a 130-fold increase in endogenous sesquiterpene production.

Notably, the transgenic plant of the present disclosure may also be genetically modified to produce exogenous terpenoids, the production of which will also be amplified using the techniques of the present disclosure. These embodiments are particularly useful where a desired terpenoid is not naturally produced by the wild-type plant. Accordingly, the transgenic plant of the present disclosure may further comprise a third heterologous nucleic acid comprising a sequence encoding a synthase for catalyzing the formation an exogenous terpene product of interest. Accordingly, in addition to producing increased amounts of endogenous terpenes due to the coexpression of HMGR/MPD and/or HMGR/PMK, the novel transgenic plant will also produce the exogenous terpene product of interest in amplified amounts as it utilizes the same biosynthesis pathway and flux therethrough is increased. In this manner, the transgenic plants of the present disclosure not only provide for the significant amplification of endogenous terpenoid production, but also the ability to produce one or more exogenous terpenes of interest in higher amounts than has been heretofore achieved using conventional methodologies.

Figure 15:
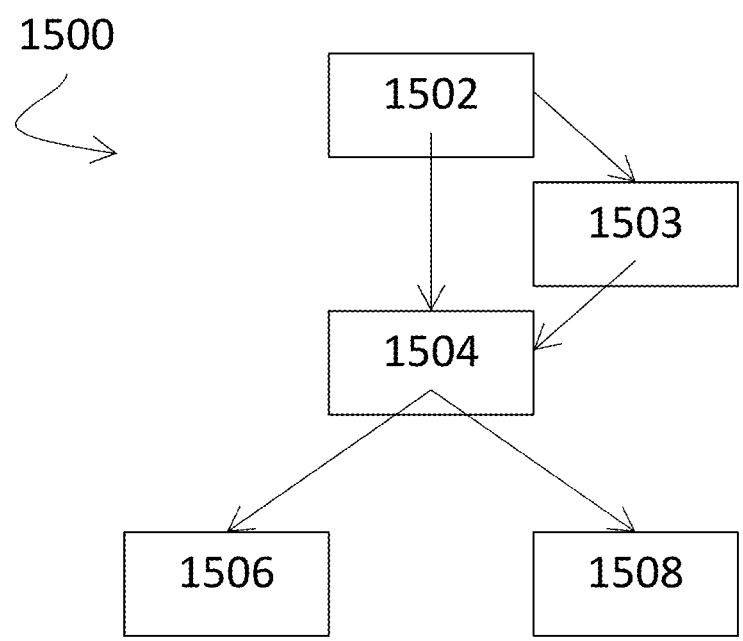
FIG. 15 shows a flow-chart representative of method 1500 for producing terpenoids using the transgenic plant and/or cells of the present disclosure.

Now referring to FIG. 15, methods for producing terpenoids using a transgenic plant are also provided in view of the disclosure provided herein. In at least one embodiment, such a method 1500 comprises a step 1502 of providing a transgenic plant or plant cells co-expressing both HMGR and MPD or PMK transgenes. For example, the transgenic plant/cells may comprise a first heterologous nucleic acid encoding a polypeptide having HMGR activity and a second heterologous nucleic acid encoding a polypeptide having MPD or PMK activity such that HMGR and the polypeptide having MPD or PMK activity are stably or transiently overexpressed in the transgenic plant as compared to a corresponding wild-type plant.

Step 1502 may be performed according to the concepts and methodologies described herein and/or using methodologies now-known in the art or hereinafter developed for the genetic manipulation of plants and plant cells. For example, and without limitation, plant cells may be transformed with a transformation vector carrying the first heterologous nucleic acid encoding a polypeptide having HMGR activity to increase HMGR enzyme content in the transgenic plant. By way of nonlimiting example, such vector may contain *Arabidopsis hmgr* under the control of a CaMV 35S promoter.

Additionally or alternatively, the plant cells are cotransformed with a bacterial MPD gene (from *Roseiflexus castenholzii*, for example) that encodes an enzyme that possesses specificity for the efficient decarboxylation of MVAP to IP and thereby introduces de novo IP formation in the transgenic plant. In at least one embodiment, the MPD gene may be stably or transiently overexpressed in the transgenic plant under the control of a CaMV 35S promoter (or the like). This creates a bifurcation in the canonical MVA pathway and allows for the production of IP without dephosphorylating IPP (similar to the alternative MVA pathway in some bacteria and archaea).

Still further, plant cells may be transformed with a vector carrying the second heterologous nucleic acid encoding a polypeptide having PMK activity to increase PMK content in the transgenic plant. By way of a nonlimiting example, such transformation vector may comprise an *Arabidopsis* PMK vector under the control of a CaMV 35S promoter.

In at least one exemplary embodiment, the transgenic plant/cells further comprises a third heterologous nucleic acid comprising a sequence encoding a synthase for catalyzing the formation of an exogenous terpene product of interest. In such cases, at step 1503, the plant and/or plant cells are transformed with a vector carrying the third heterologous nucleic acid such that the resulting transgenic plant and/or cells expresses at least a portion of the exogenous terpene product of interest. For example, in at least one embodiment, the third heterologous nucleic acid encodes *Santalum album*, *S. austrocaledonicum*, or *S. spicatum* santalene synthase, which catalyzes the formation of a mixture of sesquiterpenoids in the resulting transgenic plant.

While specific plant and bacterial species are listed herein by way of explanatory examples, such examples are not intended to be limiting. Indeed, the present disclosure should be broadly interpreted to include any other species of genes that one of ordinary skill in the art may contemplate or find beneficial in view of the findings of the present disclosure and the current state of the art.

After the transgenic plants or cells of step 1502, and optionally step 1503, are obtained, explants are selected out that contain and coexpress both the first and second heterologous nucleic acids and grown into mature plants that produce terpenoids. Where the method 1500 includes step 1503 such that transgenic plant/cells also incorporate the third heterologous nucleic acid, the selection criteria at step 1504 further includes those explants that also coexpress at least a portion of the exogenous terpene product of interest.

Perhaps more specifically, in at least one embodiment, following the transformation step(s) 1502/1503 (as desired) of method 1500, a plurality of the resulting transgenic plant cells are cultured at step 1504. A subset of transgenic plant cells that overexpress the genes of interest (e.g., HMGR+ MPD and/or PMK and, optionally, a third exogenous terpene synthesis gene) are then selected and isolated from the culture. At step 1504 such transgenic plant or cells is/are grown under desired conditions to achieve a mature transgenic plant that overexpresses HMGR and MPD or HMGR and PMK (and the exogenous terpenoid synthetase, if desired) as compared to a corresponding wild-type plant. Pursuant to the experimental data set forth herein, the coexpression of HMGR and MPD or PMK affects flux toward downstream terpenoid production and, thus, results in between about at least a 20-100 fold increase of terpenoid production as compared to a wild-type plant (and, up to or greater than a 130-fold increase of sesquiterpene production).

If desired, one or more terpenoids (endogenous or exogenous) may also be isolated and/or harvested from the transgenic plant at optional step 1506 pursuant to methodologies commonly known in the art. Additionally or alternatively, because terpenoid production in plants (e.g., crops) enhances the natural defenses of the plant, method 1500 may be leveraged as a pest and/or pathogen-management application or strategy. In such embodiments, the method 1500 further comprises optional step 1508 wherein crops comprising one or more of the transgenic plants of the present disclosure are grown in a plant growing area pursuant to methods commonly known in the art. Such crops may, in at least one embodiment, be agricultural. Furthermore, the crops may comprise seasonal or perennial plants and/or the plant growing area may comprise an outdoor field or other growing area (whether in a greenhouse or other indoor facility).

Accordingly, unlike conventional techniques, the transgenic plants and methods of the present disclosure provide for a significant increase in terpenoid production. While various embodiments of transgenic plants, platforms, and methods hereof have been described in considerable detail, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or too limiting. The scope of the disclosure is to he defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

The invention claimed is:

1. A transgenic plant comprising:
   a first heterologous nucleic acid sequence encoding a 3-hydroxy-3-methylglutarylCoA reductase (HMGR) and a second heterologous nucleic acid sequence encoding either a plant peroxisomal phosphomevalonate kinase (PMK) or an archaeal phosphomevalonate decarboxylase (MPD);
   wherein the transgenic plant overexpresses HMGR in the cytoplasm as compared to a corresponding wild-type plant and overexpresses in the peroxisome either said peroxisomal PMK or said MPD as compared to a corresponding wild-type plant.

2. The transgenic plant of claim 1, wherein the first heterologous nucleic acid sequence is from *Arabidopsis*.

3. The transgenic plant of claim 1, wherein:
   the second heterologous nucleic acid sequence encodes an archaeal MPD from *Roseiflexus castenholzii* and introduces de novo formation of isopentenyl phosphate (IP) in peroxisomes of the transgenic plant.

4. The transgenic plant of claim 1, wherein the second heterologous nucleic acid sequence encodes PMK, from *Arabidopsis*.

5. The transgenic plant of claim 3, wherein the transgenic plant produces an increased amount of metabolically available IP relative to an amount of metabolically available IP produced in a corresponding wild-type plant.

6. The transgenic plant of claim 1, further comprising at least a third nucleic acid comprising a sequence encoding a synthase for catalyzing the formation of an exogenous terpenoid product of interest, wherein the transgenic plant expresses at least a portion of the exogenous terpenoid product of interest.

7. The transgenic plant of claim 1, wherein the second heterologous nucleic acid sequence encodes said peroxisomal PMK and monoterpene and sesquiterpene production of the transgenic plant is at or near 20-fold greater and at or near 130-fold greater, respectively, than monoterpene and sesquiterpene production in the corresponding wild-type plant.

8. The transgenic plant of claim 1, wherein one or both of the first and second heterologous nucleic acid sequences is operably linked to a regulatory element for directing expression of the first and second heterologous nucleic acid sequences.

9. The transgenic plant of claim 8, wherein the regulatory element comprises a tissue-specific promoter for directing expression of the first or second heterologous nucleic acid sequence in the plant cells of a leaf, root, flower, developing ovule or seed of the transgenic plant.

10. The transgenic plant of claim 1, wherein the transgenic plant is selected from the group consisting of: tobacco, rice, flax, wheat, barley, rye, corn, potato, pea, lettuce, cabbage, cauliflower, broccoli, turnip, radish, spinach, asparagus, onion, pepper, celery, squash, pumpkin, cucumber, strawberry, grape, raspberry, blackberry, pineapple, avocado, mango, banana, soybean, tomato, sorghum, sugarcane, and algae.

11. A method for producing terpenoids using a transgenic plant comprising the steps of:
   providing a transgenic plant comprising a first heterologous nucleic acid sequence encoding 3-hydroxy-3-methylglutarylCoA reductase (HMGR) and a second heterologous nucleic acid sequence encoding phosphomevalonate decarboxylase (MPD) or phosphomevalonate kinase (PMK) such that the first heterologous nucleic acid sequence is overexpressed in a native mevalonate pathway of the transgenic plant as compared to a corresponding wild-type plant and the second heterologous nucleic acid sequence is overexpressed in the transgenic plant as compared to a corresponding wild-type plant; and
   growing the transgenic plant under desired conditions such that one or more terpenoids of interest are produced.

12. The method of claim 11, further comprising the step of isolating one or more terpenoids of interest from the transgenic plant after growth.

13. The method of claim 11, wherein the transgenic plant is grown in the presence of labeled carbon dioxide, water, or a combination thereof.

14. The method of claim 11, wherein the step of providing a transgenic plant further comprises the steps of:
   transforming plant cells with *Agrobacterium* containing a vector carrying the first heterologous nucleic acid sequence in a context that allows for the overexpression of the HMGR in a transgenic plant as compared to a corresponding wild-type plant;

transforming the plant cells with a gene containing a vector carrying the second heterologous nucleic acid sequence in a context that allows for the overexpression of PMK in the native mevalonate pathway of the transgenic plant as compared to a corresponding wild-type plant;

selecting transformants that overexpress both PMK and HMGR and growing the transformants into a transgenic plant.

15. The method of claim 11, further comprising the steps of:

transforming plant cells with a third nucleic acid sequence operably linked to one or more regulatory elements for directing expression of the third nucleic acid sequence in the plant cells, the third nucleic acid sequence encoding a synthase for catalyzing the formation an exogenous terpenoid product of interest; and selecting transformants that contain and overexpress both PMK and HMGR and that express at least a portion of the exogenous terpenoid product of interest.

16. The method of claim 11, wherein the transgenic plant produces one or more terpenoids of interest at or over a 20-fold increase relative to terpenoid production of each terpenoid of interest in a corresponding wild-type plant.

17. A method for producing a transgenic plant cell culture comprising the steps of:

obtaining transgenic plant cells by co-transforming plant cells with:

a first heterologous nucleic acid sequence encoding 3-hydroxy-3-methyl glutarylCoA reductase (HMGR) under the control of a first promoter to overexpress HMGR in a native mevalonate pathway of the transgenic plant as compared to a corresponding wild-type plant, and a second heterologous nucleic acid sequence encoding phosphomevalonate kinase (PMK) under the control of a second promoter to overexpress PMK in the native mevalonate pathway of the transgenic plant;

culturing a plurality of the transgenic plant cells; and selecting and isolating from the plurality of transgenic plant cells a subset of transgenic plant cells where expression of the first and second nucleic acid sequences are amplified as compared to wild-type resulting in a transgenic plant cell culture.

18. The method of claim 17, wherein:

the step of obtaining transgenic plant cells further comprises co-transforming the plant cells with a third nucleic acid a sequence encoding a synthase for catalyzing the formation an exogenous terpenoid product of interest;

the method further comprises the step of cultivating the transgenic plant cells so that at least a portion of the exogenous terpenoid product of interest encoded by the third nucleic acid sequence is expressed by the transgenic cells; and the subset of transgenic plant cells in the selecting and isolating step further comprises transgenic plant cells expressing at least a portion of the exogenous terpenoid product of interest.

19. The method of claim 17, wherein the transgenic plant cell culture produces β-caryophyllene and 5-epi-aristolochene at or near a 17-fold and a 63-fold increase, respectively, relative to β-caryophyllene and 5-epi-aristolochene emission in a corresponding wild-type plant cell culture.

20. The method of claim 17, further comprising the step of growing transgenic plant tissue from the subset of transgenic plant cells.

* * * * *